US006709656B1

(12) United States Patent
Boren et al.

(10) Patent No.: US 6,709,656 B1
(45) Date of Patent: Mar. 23, 2004

(54) HELICOBACTER PYLORI ADHESIN BINDING GROUP ANTIGEN

(76) Inventors: Thomas Boren, Torelvagen 68 S-906 28, Umea (SE); Anna Arnqvist, O. Brinkvagen 55 S-903, 21 Umea (SE); Lennart Hammarstrom, Avd. for Klinisk Immunologi Huddinge Sjukhus S-141, 86 Huddinge (SE); Staffan Normark, Vallhallavagen 126 S-1141, 41 Stockholm (SE); Dag Ilver, Bankgatan 18 S-902, 35 Umea (SE)

( * ) Notice: Subject to any disclaimer, the term of this patent is extended or adjusted under 35 U.S.C. 154(b) by 0 days.

(21) Appl. No.: 09/202,178

(22) PCT Filed: Jun. 10, 1997

(86) PCT No.: PCT/SE97/01009

§ 371 (c)(1),
(2), (4) Date: Feb. 10, 1999

(87) PCT Pub. No.: WO97/47646

PCT Pub. Date: Dec. 18, 1997

(30) Foreign Application Priority Data

Jun. 10, 1996 (SE) .............................................. 9602287
Mar. 19, 1997 (SE) .............................................. 9701014

(51) Int. Cl.[7] .............................................. A61K 39/02
(52) U.S. Cl. .................... 424/190.1; 424/184.1; 424/234.1; 435/7.32; 435/252.1; 530/350; 800/2; 514/25
(58) Field of Search ................... 424/234.1, 190.1, 424/184.1; 514/25; 435/7.32, 252.1; 530/350; 800/2

(56) References Cited

U.S. PATENT DOCUMENTS

| 5,538,729 A | * | 7/1996 | Czinn et al. ............. 424/234.1 |
| 5,625,124 A | * | 4/1997 | Falk et al. ..................... 800/2 |
| 5,837,502 A | * | 11/1998 | Smith ........................ 435/91.2 |
| 5,846,751 A | * | 12/1998 | Pronovost et al. ......... 435/7.32 |
| 5,883,079 A | * | 3/1999 | Zopf et al. ..................... 514/25 |
| 5,897,475 A | * | 4/1999 | Pace et al. ............... 435/252.1 |
| 6,051,416 A | * | 4/2000 | Pace et al. ............... 435/252.1 |
| 6,238,894 B1 | * | 5/2001 | Taylor et al. ............... 435/101 |
| 6,410,719 B1 | * | 6/2002 | Boren et al. ............... 536/23.7 |

FOREIGN PATENT DOCUMENTS

| FR | 2724936 | * | 9/1994 |
| WO | WO 9201718 | | 2/1992 |
| WO | 97/12908 | * | 4/1995 |

OTHER PUBLICATIONS

Smith, KR, Helicobacter sp infection in a dog in association with gastric perforation, Australian Veterinary Practitioner, vol. 26(3), Sep. 1996, pp. 140–145.*
Oriol, R. Transplantation proceedings, Dec. 1987, vol. 19(6), pp. 4416–4420, Tissular expression of ABH and Lewis antigens in humans and animals.*
McKibbin, John M et al, The Journal of Biological Chemistry, vol. 257(2), Jan. 25, 1982, pp. 755–760, Lewis Blood group fucolips and their isomers from huam and canine intestine.*

(List continued on next page.)

Primary Examiner—Lynette R. F. Smith
Assistant Examiner—Ginny Allen Portner
(74) Attorney, Agent, or Firm—Birch, Stewart, Kolasch & Birch, LLP

(57) ABSTRACT

A novel blood group antigen binding (BAB) adhesin protein was isolated and purified, whereby said protein or fractions thereof bind specifically to Helicobacter pylori fucosylated blood group antibodies. Said adhesin has a molecular weight of about 73.5 kDa and the N-terminal sequence for the adhesin and the corresponding DNA show homologies between different strains of H. pylori. Said adhesin and/or DNA is useful for diagnose and therapy and/or profylax directed against H. pylori induced infections, e.g. gastritis and acid peptic disease.

5 Claims, 10 Drawing Sheets

OTHER PUBLICATIONS

Chmiela, M et al, FEMS Immunology and Medical Microbiology, vol. 10(3–4), pp. 307–326, Feb. 1995 (abstract only).*

Lelwala–Guruge, J et al, FEMS Immunology and Medical Microbiology, vol. 11(1), pp. 73–77, Mar. 1995 (abstract only).*

Farokhnia, Mitra, Antibody specific for a plasmid encoded protein of *Helicobacter pylori*, A Thesis for the degree of master of Science in the graduate Scool of the Texas Woman's University, Dec. 1995.*

Sjostedt, S et al, Ann. Surg. Mar. 1988, vol. 207(3), pp. 341–346 (abstract).*

Blakely, JL et al, J Med Microbiol., Nov. 1982, vol. 15(4), pp. 519–529 (abstract).*

Essery, SD et al, FEMS Immunology Med. Microbiol., Jun. 1994, vol. 9(1), pp. 15–21, (abstract).*

Lelwala–Guruge, J et al, Zbl. Bakt vol. 280, pp. 93–106, 1993.*

Falk, Per. et al, Proc. Natl Acad. Sci, vol. 90, pp. 2035–2039, Mar. 1993.*

Boren, T et al, Trends in Microbiology, vol. 2(7), pp. 221–228, Jul. 1994.*

Smith, A et al, The Lancet, vol. 343 (8896), pp. 543 (abstract), Feb. 1994.*

Fauchere, JL et al, Microbial Pathogenesis, vol. 9, pp. 427–439, 1990.*

Enders, G et al, Infection Immunity, vol. 63(7), pp. 2473–2477, Jul. 1995.*

Ho, B et al, European Journal of Gastroenterology and Hepatology, vol. 7, pp. 121–124, 1995.*

Moran, A.P; FEMS Immunology and Medical Microbiology, vol. 10, pp. 271–280, 1995.*

Lingwood, CA et al, Lancet, vol. 2(8657), pp. 238–241, Jul. 29, 1989.*

Alkout, AH et al, Gut, Jul. 11–19, 1995, vol. 37(7), p. A21, abstract #84, (abstract only).*

Huang, J et al, Journal of General Microbiology, vol. 138, 1992, pp. 1503–1513.*

Amano, Ken–chi, Pathogenic factors of *Helicobacter pylori* endotoxin (LPS), English translation, Akita J. Med. vol. 24, pp. 101–108, 1997.*

Carlsson, A et al, Gastroduodenal Pathology and *Campylobacter pylori*, Oct. 7–8, 1988, Excerpta Medica, Amsterdam, 1989, pp. 375–378.*

Chan, N.W.C. et al, Glycobiology, vol. 5(7), pp. 683–688, 1995, "The Biosynthesis of Lewis X in *Helicobacter pylori*".*

Rasko, David A et al, The Journal of Biological Chemistyr, vol. 275(7), Feb. 18, 2000, pp. 4988–4994.*

Wang, G etal, Microbiology, vol. 145, pates 3245–3253, 1999.*

Ge, Z etal, The Journal of Biological Chemistry, vol. 27234), Aug. 22, 1997, pp. 21357–21363.*

Bryant, An Introduction to Immunohematology, WB Saunders Company, Second Edition, copy right 1979, 1982, pp. 34 and 91.*

Doig, P et al, Journal of Bacteriology, Vo.. 177(19), Oct. 1995, pp. 5447–5452.*

Exner, MM et al, Infection and Immunity, Vo. 63(4), pp. 1567–1572, Apr. 1995.*

Hirmo, S et al, Glycoconj. J, 1996, Dec. 13(6), pp. 1005–1011 (abstact only).*

Huang, J et al, FEMS Microbiology Letters, vol. 56(1), pp. 109–112, 1988.*

Newell, DG, Journal of General Microbiology, vol. 133, pp. 163–170.*

Jiang, Qin et al, Molecular Microbiology, vol. 20(4), pp. 833–842 "Variability of gene order in different *Helicobacer pylori* strains contributes to genome diversity".*

Science, vol. 262, Dec. 1993, Thomas Boren et al, "Attachment of *Helicobacter pylori* to Human Gastric Epithelium Mediated by Blood Group Antigens" p. 1892–1895.

Dialog Information Services, File 34, Scisearch, Dialog accession No. 15596361, Alkout AM et al; "Isolation of a Cell surface component of *Helicobacter pylori* that binds H type 2, Lewis (a), and Lewis (b) antigens", & Gastroenterology, 1997, V112, N4 (APR), P1179–1187.

Dialog Information Services, File 34, Scisearch, Dialog accession No. 15313697, Clyne M. et al; "Cell–envelope characteristics of *helicobacter–pylori*–their role in adherence to mucosal surfaces and virulence"; & Fems, Immunology and Medical Microbiology, 1996, V16, N2 (DEC 1), P141–155.

Dialog Information Service, File 34, Scisearch, Dialog accession No. 14645778, Cameron BJ et al.; "Blood–Group Glycolipids as Epithelial–Cell Receptors for *Candida–Albicans*"; & Infection and Immunity, 1996, V64, N3 (MAR), P891–896.

* cited by examiner

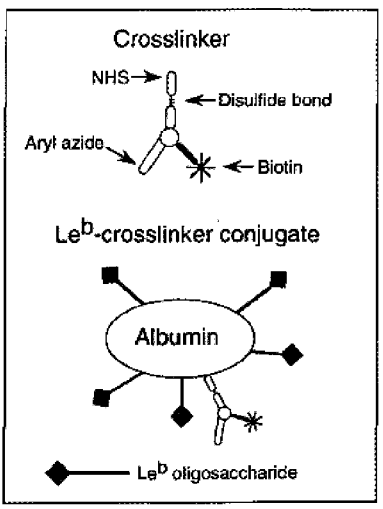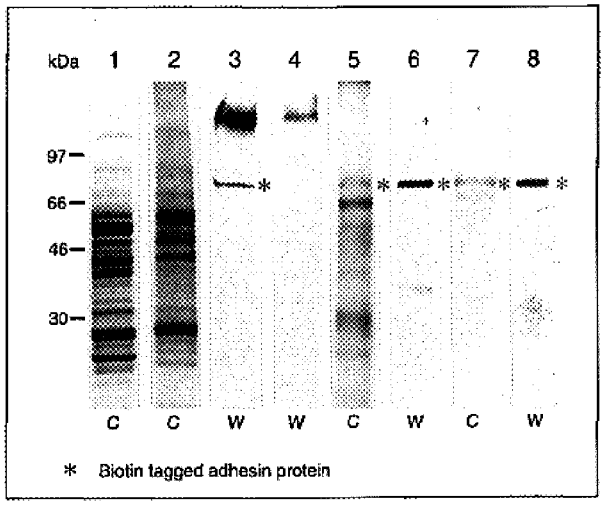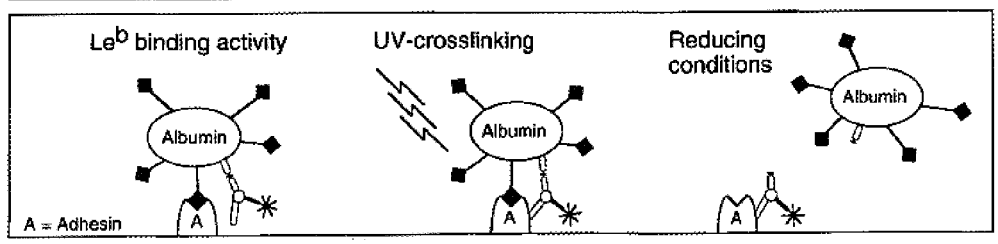

SEQUENCE LISTING

<160> NUMBER OF SEQ ID NOS: 8

<210> SEQ ID NO 1
<211> LENGTH: 3340
<212> TYPE: DNA
<213> ORGANISM: Helicobacter pylori

<400> SEQUENCE: 1

```
tttcagtcaa gcccaaagct atgcgcaaaa cgcttatgct aaagagaatt tacaagcaca      60
gccgtccaag tatcaaaaca gcgtgcctga aatcaatatt gatgaagaag aaatcccctt     120
taagggttaa aattaaggag acattatgga aagaaaacgc tattcaaaac gctattgcaa     180
atacactgaa gctaaaatca gctttattga ctataaagat ttggacatgc tcaagcacac     240
gctatcagag cgctataaaa tcatgccaag gaggttgaca ggcaatagca aaaagtggca     300
agagagggtg gaagttagcg atcaaagag cccgccacat ggctttaatc ccctacattg     360
tggataggaa aaaagtcgtg gatagccctt taaacagca ctgaatttt gattagggct       420 aataggggc atgcctttta atcttgttta atcttggctc tattttgtt aaacatcggt        480 tataaaagcg ttaaagcac ttttaaatc caattaaaag cgttcaaaag taacgcaaaa        540
aatcaaaaaa atgacaaaat ttttaagaaa atgacaaaaa aaaaaaaaac gctttatgct      600
ataatattcc aaatacattc taatgcaaat gcattctaat gcaaatgtat aatgaatgta      660
tgaaatccct aatattcaat ccaatttaat ccaaaaagga gaaaaacac atcctttcat      720 taactttagg ctcgctttta gtttccactt tgagcgctga agacgacggc ttttacacaa     780
gcgtaggcta tcaaatcggt gaagccgctc aaatggtaac aaacaccaaa ggcatccaag     840
atctttcaga caactatgaa aacttgagca aactttgac ccgatacagc accctaaaca       900
cccttatcaa attgtccgct gatccgagcg cgattaacgc ggcacgtgaa aatctgggcg     960
```

-continued

```
cgagcgcgaa gaacttgatc ggcgatacca aaaattcccc cgcctatcaa gccgtgcttt     1020
tggcgatcaa tgcggcggta gggttttgga atgtcttagg ctatgctacg caatgcgggg     1080
gtaacgctaa tggtcaagaa agcacctctt caaccaccat cttcaacaac gagccagggt     1140
atcgatccac ttccatcact tgcagtttga acaggtataa gcctggatac tacgccccta     1200
tgagcattga aaatttcaaa aagcttaacg aagcctatca aatcctccaa acggctttaa     1260
ataaaggctt acccgcgctc aaagaaaaca acggaacggt cagtgtaacc tacacctaca     1320
catgctcagg ggaagggaat gataactgct cgaaaaaagc cacaggtgta agtgaccaaa     1380
atggcggaac caaaactaaa acccaaacca tagacggcaa aaccgtaacc accacgatca     1440
gttcaaaagt cgttgatagt caggcaaaag gtaatacaac aagggtgtcc tacaccgaaa     1500
tcactaacaa attagacggt gtgcctgata gcgctcaagc gctcttggcg caagcgagca     1560
cgctcatcaa caccatcaac acggcatgcc cgtattttag tgtaactaat aaaagtggtg     1620
gtccacagat ggaaccgact agagggaagt tgtgcggttt tacagaagaa atcagcgcga     1680
tccaaaagat gatcacagac gcgcaagagc tggtcaatca aacgagcgtc attaacgagc     1740
atgaacaatc aaccccggta ggcggtaata atggcaagcc tttcaaccct ttcacggacg     1800
caagcttcgc tcaaggcatg ctcgctaacg ctagtgcgca agccaaaatg ctcaatctag     1860
cccatcaagt ggggcaaacc attaaccctg acaatcttac cgggactttt aaaaattttg     1920
ttacaggctt tttagccaca tgcaacaaca aatcaacagc tggcactagt ggcacacaag     1980
gttcacctcc tggcacagta accactcaaa cttccgcttc cggttgcgcc tatgtggagc     2040
aaaccataac gaatctaaac aacagcatcg ctcattttgg cactcaagag cagcagatac     2100
agcaagctga aaacatcgct gacactctag tgaatttcaa atctagatac agcgaattag     2160
ggaatactta taacagcatc actactgcgc tctccaaagt ccctaacgcg caaagcttgc     2220
aaaacgtggt gggaaaaaag aataacccct atagcccgca aggcatagaa accaattact     2280
acttgaatca aaactcttac aaccaaatcc aaaccatcaa ccaagaatta gggcgtaacc     2340
cctttaggaa agtgggcatc gtcagttctc aaaccaacaa tggtgccatg aatgggatcg     2400
gtatccaggt gggctacaag caattctttg ggcaaaaaag gaaatggggt gcaagatact     2460
acggcttttt tgattacaac catgcgttca ttaaatccag cttcttcaac tcggcttctg     2520
acgtgtggac ttatggtttt ggagcggacg ctctttataa cttcatcaac gataaagcca     2580
ccaatttctt aggcaaaaac aacaagcttt ctgtggggct ttttggcggg attgcgttag     2640
cgggcacttc atggcttaat tctgaatacg tgaatttagc caccatgaat aacgtctata     2700
acgctaaaat gaacgtggcg aacttccaat tcttattcaa catgggagtg aggatgaatt     2760
tagccagatc caagaaaaaa ggcagcgatc atgcggctca gcatggcatt gagttagggc     2820
ttaaaatccc caccattaac acgaactact attcctttat gggggctgaa ctcaaatacc     2880
gcaggctcta tagcgtgtat ttgaattatg tgttcgctta ctaaaaacta aaaatccttt     2940
gtggaactcc cttttaagg ggtttctttt aaagccttta ttttttttg gagggttta     3000 atttttttga aacctttgtt tttgaattct cttttaatg ggtttctttt ttgaactctt     3060
tgttttgaac tccttttttt gaactccctt ttttaaaccc tttctttttt aaaattctct     3120
tttttggggg gtttgatgaa aaatccttt ttagcgtttt ggtattggtt agtggaaaac     3180
ttgatactaa ttttaagcgat agtttttaaa aagtgcttct ttaatatagg gggtttaagt     3240
tggtgattaa aaggggggaa tggtttcaaa gcgcttccta tccctttaag aaaataaaat     3300
```

-continued

| aaaactttaa taaaatgagt tttacaacaa aatgagatcc | 3340 |

<210> SEQ ID NO 2
<211> LENGTH: 2781
<212> TYPE: DNA
<213> ORGANISM: Helicobacter pylori

<400> SEQUENCE: 2

| catttgatcg cattggattt caaagaaggg cgttttgtga aaggctttgg tcaagcttat | 60 |
| gatattttag gcgacaaaat cgcttatgtt ggggtaaag gcaacccaca caatttcgct | 120 |
| cacaagaaat aaactttctc acccataagg ggcaaacgcc cccaaaagag tgctttttaa | 180 |
| agaggttaag gcaaaatcaa gctctttagt atttaatctt aaaaaatact aaagcctttt | 240 |
| ttatgggcta acaccacaca aaagcgtca aaatcaaaaa aatgacaaaa ttttccccaa | 300 |
| atgacaaaaa aaaaaaaaaa cgattttatg ctatattaac gaaatcttgt gataagatct | 360 |
| tattcttta aaagatttac ctaaccattt taatttcaag gagaaaacat gaaaaaaaac | 420 |
| cctttactc tctctctctc tctctcgttt ttgctccacg ctgaagacga cggcttttac | 480 |
| acaagcgtag gctatcaaat cggtgaagcc gctcaaatgg taaccaacac caaaggcatc | 540 |
| caacagcttt cagacaatta tgaaaagctg aacaatcttt tgaataatta cagcacccta | 600 |
| aacacccta tcaaattatc cgctgatccg agtgcgatta acgacgcaag ggataatcta | 660 |
| ggctcaagtg ctaagaattt gcttgatgtt aaaaccaact ccccggccta tcaagccgtg | 720 |
| cttttagcgt tgaatgcggc ggtgggttg tggcaagtta caagctacgc ttttactgct | 780 |
| tgtggtcctg gcagtaacga gagcgcaaat ggaggtatcc aaacttttaa taatgtgcca | 840 |
| ggacaaaaga cgacaaccat cacttgcaat tcgtattatc aaccaggaca tggtgggcct | 900 |
| atatccactg caaactatgc aaaaatcaat caagcctatc aaatcattca aaaggctttg | 960 |
| acagccaatg aagctaatgg agatggggtc cccgttttaa gcgacaccac tacaaaactt | 1020 |
| gatttcacta ttcaaggaga caaagaacg ggtggccgac caaatacacc taaaaagttc | 1080 |
| ccatggagtg atgggaaata tattcacacc caatggattg acacaacacc acaatcaaca | 1140 |
| gaaacaaaga tcaacacaga aaataacgct caagagcttt taaacaagc gagcatcatt | 1200 |
| atcactaccc taaatgaggc atgcccaaac ttccaaaatg gtggtagcgg ttattggcaa | 1260 |
| gggataagcg gcaatgggac aatgtgtggg atgtttaaga atgaaatcag cgctatccaa | 1320 |
| ggcatgatcg ctaacgcgca agaagctgtc gcgcaaagta aaatcgttag tgaaaatgcg | 1380 |
| caaaatcaaa acaacttgga tactggaaaa ccattcaacc ctttcacgga cgctagcttc | 1440 |
| gctcaaagca tgctcaaaaa cgctcaagcc caagcagaga ttttaaacca agccgaacaa | 1500 |
| gtggtgaaaa actttgaaaa aatccctaaa aattttgtat cagactcttt agggtgtgt | 1560 |
| tatgaagagc aaggggtga gcgtagggc accaatccag gtcaggttac ttctaacact | 1620 |
| ttcgcttccg gttgcgccta tgtggagcaa accataacga atctaaacaa cagcatcgct | 1680 |
| cattttggca ctcaagagca gcagatacag caagctgaaa acatcgctga cactctagtg | 1740 |
| aatttcaaat ctagatacag cgaattaggg aatacttata cagcatcac tactgcgctc | 1800 |
| tccaaagtcc ctaacgcgca aagcttgcaa acgtggtgg gaaaaagaa taacccctat | 1860 |
| agcccgcaag gcatagaaac caattactac ttgaatcaaa actcttacaa ccaaatccaa | 1920 |
| accatcaacc aagaattagg gcgtaacccc tttaggaaag tgggcatcgt cagttctcaa | 1980 |
| accaacaatg gtgccatgaa tgggatcggt atccaggtgg gctacaagca attctttggg | 2040 |
| caaaaaagga atgggggtgc aagatactac ggcttttttg attacaacca tgcgttcatt | 2100 |

-continued

```
aaatccagct tcttcaactc ggcttctgac gtgtggactt atggttttgg agcggacgct    2160
ctttataact tcatcaacga taaagccacc aatttcttag gcaaaaacaa caagctttct    2220
gtggggcttt ttggcgggat tgcgttagcg ggcacttcat ggcttaattc tgaatacgtg    2280
aatttagcca ccatgaataa cgtctataac gctaaaatga acgtggcgaa cttccaattc    2340
ttattcaaca tgggagtgag gatgaattta gccagatcca agaaaaaagg cagcgatcat    2400
gcggctcagc atggcattga gttagggctt aaaatcccca ccattaacac gaactactat    2460
tcctttatgg gggctgaact caaataccgc aggctctata gcgtgtattt gaattatgtg    2520
ttcgcttact agaaactaaa aatcctttgt ggaactccct ttttaagggg tttcttttaa    2580
agcctttatt ttttttgga ggggtttaat tttttgaaa cctttgtttt tgaattctct    2640
ttttaatggg tttcttttt gaactctttg ttttgaactc cttttttga actccctttt    2700 ttaaacccctt tctttttaa aattctcttt tttgggggt ttgatgaaaa atcctttttt    2760
agcgttttgg tattggttag t                                              2781
```

```
<210> SEQ ID NO 3
<211> LENGTH: 744
<212> TYPE: PRT
<213> ORGANISM: Helicobacter pylori
<220> FEATURE:
<221> NAME/KEY: PEPTIDE
<222> LOCATION: (24)..(64)
<223> OTHER INFORMATION: N-terminal domain of the BabA adhesin

<400> SEQUENCE: 3

Ser Lys Lys Glu Lys Lys His Ile Leu Ser Leu Thr Leu Gly Ser Leu
  1               5                  10                  15

Leu Val Ser Thr Leu Ser Ala Glu Asp Asp Gly Phe Tyr Thr Ser Val
                 20                  25                  30

Gly Tyr Gln Ile Gly Glu Ala Ala Gln Met Val Thr Asn Thr Lys Gly
             35                  40                  45

Ile Gln Asp Leu Ser Asp Asn Tyr Glu Asn Leu Ser Lys Leu Leu Thr
         50                  55                  60

Arg Tyr Ser Thr Leu Asn Thr Leu Ile Lys Leu Ser Ala Asp Pro Ser
 65                  70                  75                  80

Ala Ile Asn Ala Ala Arg Glu Asn Leu Gly Ala Ser Ala Lys Asn Leu
                 85                  90                  95

Ile Gly Asp Thr Lys Asn Ser Pro Ala Tyr Gln Ala Val Leu Leu Ala
            100                 105                 110

Ile Asn Ala Ala Val Gly Phe Trp Asn Val Leu Gly Tyr Ala Thr Gln
            115                 120                 125

Cys Gly Gly Asn Ala Asn Gly Gln Glu Ser Thr Ser Ser Thr Thr Ile
            130                 135                 140

Phe Asn Asn Glu Pro Gly Tyr Arg Ser Thr Ser Ile Thr Cys Ser Leu
145                 150                 155                 160

Asn Arg Tyr Lys Pro Gly Tyr Tyr Gly Pro Met Ser Ile Glu Asn Phe
                165                 170                 175

Lys Lys Leu Asn Glu Ala Tyr Gln Ile Leu Gln Thr Ala Leu Asn Lys
            180                 185                 190

Gly Leu Pro Ala Leu Lys Glu Asn Asn Gly Thr Val Ser Val Thr Tyr
            195                 200                 205

Thr Tyr Thr Cys Ser Gly Glu Gly Asn Asp Asn Cys Ser Lys Lys Ala
            210                 215                 220
```

-continued

```
Thr Gly Val Ser Asp Gln Asn Gly Gly Thr Lys Thr Lys Thr Gln Thr
225                 230                 235                 240

Ile Asp Gly Lys Thr Val Thr Thr Ile Ser Ser Lys Val Val Asp
            245                 250                 255

Ser Gln Ala Lys Gly Asn Thr Thr Arg Val Ser Tyr Thr Glu Ile Thr
                260                 265                 270

Asn Lys Leu Asp Gly Val Pro Asp Ser Ala Gln Ala Leu Leu Ala Gln
            275                 280                 285

Ala Ser Thr Leu Ile Asn Thr Ile Asn Thr Ala Cys Pro Tyr Phe Ser
    290                 295                 300

Val Thr Asn Lys Ser Gly Gly Pro Gln Met Glu Pro Thr Arg Gly Lys
305                 310                 315                 320

Leu Cys Gly Phe Thr Glu Glu Ile Ser Ala Ile Gln Lys Met Ile Thr
                325                 330                 335

Asp Ala Gln Glu Leu Val Asn Gln Thr Ser Val Ile Asn Glu His Glu
            340                 345                 350

Gln Ser Thr Pro Val Gly Gly Asn Asn Gly Lys Pro Phe Asn Pro Phe
        355                 360                 365

Thr Asp Ala Ser Phe Ala Gln Gly Met Leu Ala Asn Ala Ser Ala Gln
370                 375                 380

Ala Lys Met Leu Asn Leu Ala His Gln Val Gly Gln Thr Ile Asn Pro
385                 390                 395                 400

Asp Asn Leu Thr Gly Thr Phe Lys Asn Phe Val Thr Gly Phe Leu Ala
            405                 410                 415

Thr Cys Asn Asn Lys Ser Thr Ala Gly Thr Ser Gly Thr Gln Gly Ser
        420                 425                 430

Pro Pro Gly Thr Val Thr Thr Gln Thr Phe Ala Ser Gly Cys Ala Tyr
        435                 440                 445

Val Glu Gln Thr Ile Thr Asn Leu Asn Asn Ser Ile Ala His Phe Gly
    450                 455                 460

Thr Gln Glu Gln Gln Ile Gln Gln Ala Glu Asn Ile Ala Asp Thr Leu
465                 470                 475                 480

Val Asn Phe Lys Ser Arg Tyr Ser Glu Leu Gly Asn Thr Tyr Asn Ser
            485                 490                 495

Ile Thr Thr Ala Leu Ser Lys Val Pro Asn Ala Gln Ser Leu Gln Asn
        500                 505                 510

Val Val Gly Lys Lys Asn Asn Pro Tyr Ser Pro Gln Gly Ile Glu Thr
    515                 520                 525

Asn Tyr Tyr Leu Asn Gln Asn Ser Tyr Asn Gln Ile Gln Thr Ile Asn
530                 535                 540

Gln Glu Leu Gly Arg Asn Pro Phe Arg Lys Val Gly Ile Val Ser Ser
545                 550                 555                 560

Gln Thr Asn Asn Gly Ala Met Asn Gly Ile Gly Ile Gln Val Gly Tyr
            565                 570                 575

Lys Gln Phe Phe Gly Gln Lys Arg Lys Trp Gly Ala Arg Tyr Tyr Gly
                580                 585                 590

Phe Phe Asp Tyr Asn His Ala Phe Ile Lys Ser Ser Phe Asn Ser
            595                 600                 605

Ala Ser Asp Val Trp Thr Tyr Gly Phe Gly Ala Asp Ala Leu Tyr Asn
        610                 615                 620

Phe Ile Asn Asp Lys Ala Thr Asn Phe Leu Gly Lys Asn Asn Lys Leu
625                 630                 635                 640

Ser Val Gly Leu Phe Gly Gly Ile Ala Leu Ala Gly Thr Ser Trp Leu
```

```
                    645                 650                 655
Asn Ser Glu Tyr Val Asn Leu Ala Thr Met Asn Asn Val Tyr Asn Ala
                660                 665                 670

Lys Met Asn Val Ala Asn Phe Gln Phe Leu Phe Asn Met Gly Val Arg
            675                 680                 685

Met Asn Leu Ala Arg Ser Lys Lys Gly Ser Asp His Ala Ala Gln
        690                 695                 700

His Gly Ile Glu Leu Gly Leu Lys Ile Pro Thr Ile Asn Thr Asn Tyr
705                 710                 715                 720

Tyr Ser Phe Met Gly Ala Glu Leu Lys Tyr Arg Arg Leu Tyr Ser Val
                725                 730                 735

Tyr Leu Asn Tyr Val Phe Ala Tyr
                740

<210> SEQ ID NO 4
<211> LENGTH: 707
<212> TYPE: PRT
<213> ORGANISM: Helicobacter pylori
<220> FEATURE:
<221> NAME/KEY: PEPTIDE
<222> LOCATION: (46)..(59)
<223> OTHER INFORMATION: Corresponding to the N-terminal domain of the
      BabA adhesin

<400> SEQUENCE: 4

Met Lys Lys Asn Pro Phe Thr Leu Ser Leu Ser Leu Ser Phe Leu Leu
  1               5                  10                  15

His Ala Glu Asp Asp Gly Phe Tyr Thr Ser Val Gly Tyr Gln Ile Gly
                 20                  25                  30

Glu Ala Ala Gln Met Val Thr Asn Thr Lys Gly Ile Gln Gln Leu Ser
             35                  40                  45

Asp Asn Tyr Glu Lys Leu Asn Asn Leu Leu Asn Asn Tyr Ser Thr Leu
         50                  55                  60

Asn Thr Leu Ile Lys Leu Ser Ala Asp Pro Ser Ala Ile Asn Asp Ala
 65                  70                  75                  80

Arg Asp Asn Leu Gly Ser Ser Ala Lys Asn Leu Leu Asp Val Lys Thr
                 85                  90                  95

Asn Ser Pro Ala Tyr Gln Ala Val Leu Leu Ala Leu Asn Ala Ala Val
            100                 105                 110

Gly Leu Trp Gln Val Thr Ser Tyr Ala Phe Thr Ala Cys Gly Pro Gly
        115                 120                 125

Ser Asn Glu Ser Ala Asn Gly Gly Ile Gln Thr Phe Asn Asn Val Pro
130                 135                 140

Gly Gln Lys Thr Thr Thr Ile Thr Cys Asn Ser Tyr Tyr Gln Pro Gly
145                 150                 155                 160

His Gly Gly Pro Ile Ser Thr Ala Asn Tyr Ala Lys Ile Asn Gln Ala
                165                 170                 175

Tyr Gln Ile Ile Gln Lys Ala Leu Thr Ala Asn Glu Ala Asn Gly Asp
            180                 185                 190

Gly Val Pro Val Leu Ser Asp Thr Thr Thr Lys Leu Asp Phe Thr Ile
        195                 200                 205

Gln Gly Asp Lys Arg Thr Gly Gly Arg Pro Asn Thr Pro Lys Lys Phe
    210                 215                 220

Pro Trp Ser Asp Gly Lys Tyr Ile His Thr Gln Trp Ile Asp Thr Thr
225                 230                 235                 240

Pro Gln Ser Thr Glu Thr Lys Ile Asn Thr Glu Asn Asn Ala Gln Glu
```

```
                   245                 250                 255
Leu Leu Lys Gln Ala Ser Ile Ile Thr Thr Leu Asn Glu Ala Cys
            260                 265                 270

Pro Asn Phe Gln Asn Gly Gly Ser Gly Tyr Trp Gln Gly Ile Ser Gly
            275                 280                 285

Asn Gly Thr Met Cys Gly Met Phe Lys Asn Glu Ile Ser Ala Ile Gln
            290                 295                 300

Gly Met Ile Ala Asn Ala Gln Glu Ala Val Ala Gln Ser Lys Ile Val
305                 310                 315                 320

Ser Glu Asn Ala Gln Asn Gln Asn Asn Leu Asp Thr Gly Lys Pro Phe
                325                 330                 335

Asn Pro Phe Thr Asp Ala Ser Phe Ala Gln Ser Met Leu Lys Asn Ala
            340                 345                 350

Gln Ala Gln Ala Glu Ile Leu Asn Gln Ala Glu Gln Val Val Lys Asn
            355                 360                 365

Phe Glu Lys Ile Pro Lys Asn Phe Val Ser Asp Ser Leu Gly Val Cys
370                 375                 380

Tyr Glu Gln Gly Gly Glu Arg Arg Gly Thr Asn Pro Gly Gln Val
385                 390                 395                 400

Thr Ser Asn Thr Phe Ala Ser Gly Cys Ala Tyr Val Glu Gln Thr Ile
            405                 410                 415

Thr Asn Leu Asn Asn Ser Ile Ala His Phe Gly Thr Gln Glu Gln Gln
            420                 425                 430

Ile Gln Gln Ala Glu Asn Ile Ala Asp Thr Leu Val Asn Phe Lys Ser
            435                 440                 445

Arg Tyr Ser Glu Leu Gly Asn Thr Tyr Asn Ser Ile Thr Thr Ala Leu
            450                 455                 460

Ser Lys Val Pro Asn Ala Gln Ser Leu Gln Asn Val Val Gly Lys Lys
465                 470                 475                 480

Asn Asn Pro Tyr Ser Pro Gln Gly Ile Glu Thr Asn Tyr Tyr Leu Asn
                485                 490                 495

Gln Asn Ser Tyr Asn Gln Ile Gln Thr Ile Asn Gln Glu Leu Gly Arg
            500                 505                 510

Asn Pro Phe Arg Lys Val Gly Ile Val Ser Ser Gln Thr Asn Asn Gly
            515                 520                 525

Ala Met Asn Gly Ile Gly Ile Gln Val Gly Tyr Lys Gln Phe Phe Gly
            530                 535                 540

Gln Lys Arg Lys Trp Gly Ala Arg Tyr Tyr Gly Phe Phe Asp Tyr Asn
545                 550                 555                 560

His Ala Phe Ile Lys Ser Ser Phe Phe Asn Ser Ala Ser Asp Val Trp
                565                 570                 575

Thr Tyr Gly Phe Gly Ala Asp Ala Leu Tyr Asn Phe Ile Asn Asp Lys
            580                 585                 590

Ala Thr Asn Phe Leu Gly Lys Asn Asn Lys Leu Ser Val Gly Leu Phe
            595                 600                 605

Gly Gly Ile Ala Leu Ala Gly Thr Ser Trp Leu Asn Ser Glu Tyr Val
            610                 615                 620

Asn Leu Ala Thr Met Asn Asn Val Tyr Asn Ala Lys Met Asn Val Ala
625                 630                 635                 640

Asn Phe Gln Phe Leu Phe Asn Met Gly Val Arg Met Asn Leu Ala Arg
                645                 650                 655

Ser Lys Lys Lys Gly Ser Asp His Ala Ala Gln His Gly Ile Glu Leu
            660                 665                 670
```

-continued

```
Gly Leu Lys Ile Pro Thr Ile Asn Thr Asn Tyr Tyr Ser Phe Met Gly
            675                 680                 685

Ala Glu Leu Lys Tyr Arg Arg Leu Tyr Ser Val Tyr Leu Asn Tyr Val
        690                 695                 700

Phe Ala Tyr
705

<210> SEQ ID NO 5
<211> LENGTH: 20
<212> TYPE: PRT
<213> ORGANISM: Helicobacter pylori

<400> SEQUENCE: 5

Glu Asp Asp Gly Phe Tyr Thr Ser Val Gly Tyr Gln Ile Gly Glu Ala
  1               5                  10                  15

Ala Gln Met Val
            20

<210> SEQ ID NO 6
<211> LENGTH: 60
<212> TYPE: DNA
<213> ORGANISM: Helicobacter pylori

<400> SEQUENCE: 6
gaagacgacg gcttttacac aagcgtaggc tatcaaatcg gtgaagccgc tcaaatggta    60

<210> SEQ ID NO 7
<211> LENGTH: 41
<212> TYPE: PRT
<213> ORGANISM: Helicobacter pylori

<400> SEQUENCE: 7

Glu Asp Asp Gly Phe Tyr Thr Ser Val Gly Tyr Gln Ile Gly Glu Ala
  1               5                  10                  15

Ala Gln Met Val Thr Asn Thr Lys Gly Ile Gln Asp Leu Ser Asp Asn
            20                  25                  30

Tyr Glu Asn Leu Ser Lys Leu Leu Thr
            35                  40

<210> SEQ ID NO 8
<211> LENGTH: 20
<212> TYPE: PRT
<213> ORGANISM: Helicobacter pylori

<400> SEQUENCE: 8

Glu Asp Asp Gly Phe Tyr Thr Ser Val Gly Tyr Gln Ile Gly Glu Ala
  1               5                  10                  15

Ala Gln Met Val
            20
```

HELICOBACTER PYLORI ADHESIN BINDING GROUP ANTIGEN

This application is the national phase under 35 U.S.C. §371 of prior PCT International Application No. PCT/SE97/01009 which has an International filing date of Jun. 10, 1997 which designated the United States of America.

FIELD OF THE INVENTION

The present invention relates to materials and methods for prevention, treatment and diagnosing of infections caused by *Helicobacter pylori*. More specifically the present invention relates to polypeptides and antibodies useful in vaccines for the treatment and prevention of pathologic infections caused by *Helicobacter pylori* strains. The present invention specifically relates to a bacterial blood group antigen binding adhesin (BAB-adhesin). The present invention further relates to polynucleotides useful for the recombinant production of said polypeptides and for use in immunisation therapies. In addition, it relates to polypeptides, antibodies, and polynucleotides used for the detection of said bacteria.

The present invention further relates to new immunoglobulins, which exhibit specific activity to a blood group binding adhesin, expressed by *Helicobacter pylori*, methods for the production of said immunoglobulins, their isolation and use. The present invention further relates to the treatment and prevention of *H. pylori* induced infections in the gastrointestinal tract.

BACKGROUND OF THE INVENTION

*Helicobacter pylori* is a causative agent for acid peptic disease and the presence of this organism is highly correlated to the development of gastric adenocarcinoma. Bacterial adherence to the human gastric epithelial lining was recently shown to be mediated by fucosylated blood group antigens.

Recent research has focused on the role of *Helicobacter pylori* in the development of ulcers in the gastric mucosa. Recent findings show a strong connection between *H. pylori* and chronic, active gastritis and gastric ulcers. Furthermore, there appears to be a strong correlation between ventricular cancer and gastric ulcers. Traditional treatment of gastric ulcers has involved gastric resection, the administration of bismuth compositions, the administration of $H_2$-blockers and the administration of pH-buffering agents, to mention a few examples.

More recently, various forms of treatment have been supplemented with the administration of antibiotics. One problem with presently known treatments is the risk for treatment failure. Furthermore, not only do microbes develop antibiotic resistance, the antibiotics administered often upset the natural balance of benign microbes, colonising the intestinal tract. This leads to diarrhoea and other signs of intestinal discomfort, in addition to destabilising the benign flora in the intestines. Other treatments, e.g. $H_2$-blockers often require life-long medication to prevent the recurrence of disease.

The foregoing, together with the fact that *H. pylori* is very widely spread among humans—according to a conservative estimate approximately 60% of all adult humans in the industrialised countries are infected—makes the diagnosing, prevention and treatment of *H. pylori* infections an urgent task.

Further, the fact that developing countries frequently lack the resources for conventional treatment of gastric ulcers further underlines the importance of finding new ways of treatment and prevention of *H. pylori* induced infections. It is obvious, for many reasons, that disease prevention with vaccines is a preferable mode. A vaccine would provide an easily administered and economical prophylactic regimen against *H. pylori* infections. An effective vaccine against *H. pylori* is nevertheless presently lacking.

STATE OF THE ART

*H. pylori* colonises the human gastric mucosa, in an equilibrium between adherence to the epithelial surface mucous cells and the mucous layer lining the gastric epithelium. Once infected, bacteria seems to colonise for a lifetime. Attachment to the epithelial lining protects the bacteria from the anti-microbial effects of the acidic gastric juice of the stomach lumen, as well as from physical forces such as peristalsis. For survival in this hostile ecological niche, *H. pylori* has developed a battery of virulence factors; such as production of the enzyme urease that buffers the micro-environment around the bacteria and the polar flagellae to ensure high motility, a prerequisite in an ecological niche where the turnover of the mucous layer is in the range of hours. A subset of *H. pylori* strains produces the vacuolating cytotoxin, VacA, and the cytotoxin associated antigen CagA.

Attachment is essential for colonisation of the epithelial lining and bacteria express surface associated adhesion molecules that recognise specific carbohydrate or protein receptors on the cell surfaces or mucous lining. The specificity in this interaction in combination with the genetically regulated receptor distribution results in a restricted range of cell lineages and tissues available for colonisation. Several putative receptor structures have been described for *H. pylori*, such as the hemagglutinin-sialic acid, sulphated glycoconjugates and sulphatides. Recently, the fucosylated blood group antigens H-1 and Lewis$^b$ were described (Borén et al., Science, 262, 18921993), mediating specific adherence of *H. pylori* to human and rhesus monkey gastric surface mucous cells in situ. The H-1 and Lewis$^b$ antigens are part of the blood group antigens that define blood group O in the ABO system.

Surface-exposed proteins are often constituents of the outer membrane. The outer membrane has a structural role and acts as a selective barrier, determining what enters the cell and what molecules are secreted. One class of outer membrane proteins are called porins, and create hydrophilic pores through the outer membrane where specific metabolites, such as sugar molecules, can cross. Recently the finding of a number of outer membrane proteins in *H. pylori*, was reported, which proteins were suggested to constitute a family of porin proteins.

The BAB adhesin has previously been identified and shown to be localised on the bacterial surface of *H. pylori* (SE 9602287-6). The blood group binding activity was shown to be pH dependent and the present inventors present evidence that the binding affinity to the Lewis$^b$ receptor reveals a high equilibrium constant. For the purification of the BAB adhesin, a crosslinker-labelled receptor conjugate was used in order to mediate specific transfer of biotin to the adhesins on the bacterial surface. Thereafter the biotin-labelled adhesin could be extracted by streptavidin coated magnetic beads. Determination of the amino terminal amino acid sequence of the purified BAB adhesin exhibit homologies to outer membrane proteins of *H. pylori* porins.

Intensive research has been directed to the immunological treatment and prevention of *H. pylori* induced infections. EP 0 484 148 (Ando & Nakamura) describes a method for treating and/or preventing upper gastrointestinal disease in mammals, said method comprising orally administering to a patient in need thereof an effective amount of a pharmaceutical composition comprising anti-*Helicobacter pylori* polyclonal immunoglobulins and a pharmaceutically acceptable carrier. Said description further dwells on the combination of said treatment in combination with the administration of antibiotics. As the method of producing said polyclonal antibodies, EP 0 484 148 describes the isolation and purification of anti-*H. pylori* immunoglobulins from the sera and milk of mammals. *H. pylori* itself was not found in the stomachs of cows, goats, sheep, swine or horses, according to EP 0 484 148, but it was assumed that these animal species have colonizing microorganisms with antigenic determinants similar to those of *H. pylori* because they have immunoglobulins which cross-react to strains of *H. pylori* found in humans. Preferably, according to EP 0 484 148, large mammals, e.g. pregnant cows, are immunized with whole cells of *H. pylori* and the immunoglobulins subsequently extracted from the milk or colostrum. In the immunization experiments, NCTC Strain 11362 and clinical isolate *H. pylori* No. 153 were used to trigger the production of immunoglobulins. On the other hand, NCTC Strain 11637 was used for analysing purposes. Immunization is claimed to yield an anti-*H. pylori* titer in the milk of such magnitude, that daily doses of 0.01–0.1 g/day immunoglobulin composition, are sufficient for successful therapy. The claimed interval of 0.01–0.1 g/day is however not supported by the experiments presented by Ando & Nakamura and so low doses have hitherto not proven efficient in clinical tests. The doses actually used in example 5 and 7 are in the order of magnitude of 1 g/day, i.e. 10-fold the upper limit of the given interval. Furthermore, it is very unlikely, that unspecific immunoglobulin mixtures as those manufactured by Ando & Nakamura, would be effective in claimed doses as similar doses are ineffective against other gastrointestinal pathogens. The simultaneous administration of antibiotics, extensively discussed in the description, underlines the insufficiency of the disclosed immunoglobulins.

EP 0 469 359 (Cordle & Schaller) likewise describes the immunization of mammals, preferably pregnant cows, with formalin killed *H. pylori* bacteria (ATCC Strain 26695). Anti-*H. pylori* polyclonal antibodies were isolated and purified from the milk and finally fed to piglets, in amounts of about 0.5 g immunoglobulins, three times daily. The results were assessed by determination of the number of biopsy specimens, which were positive for Gram-negative bacteria after the trial. Gram-negative bacteria was found in 78% of the piglets fed a non-immune nutrient but only (Sic!) in 35% of the piglets fed a nutrient containing so called specific anti-*H. pylori* antibodies.

Anti-*H. pylori* polyclonal antibodies, effective to cause aggregation of *H. pylori*, have thus been administered orally as a regimen in the treatment and prevention of *H. pylori* induced infections in the gastrointestinal tract. Nevertheless, as also noted in EP 0 484 148 A1, it is still not clear, how many antigenic determinants are present on the surface of *H. pylori*. The occurrence of a wide variety of *H. pylori* strains, makes questionable the practical efficiency of any polyclonal immunological therapy according to the state of the art. Immunization using whole bacteria will always trigger a highly polyclonal immunresponse with a low level of antibodies against a given antigenic determinant. This is underlined e.g. by the results presented by Cordle & Schaller, where, although the number of Helicobacter positive biopsies were reduced, complete cure was not obtained through the treatment according to their invention.

It is notable, that the dose of immunoglobulin needed for oral prophylaxis or therapy has not yet been clearly defined. In a normal human adult, approximately 5 g IgA is produced and secreted at mucosal surfaces each day. Obviously, doses of this magnitude are economically and practically unfeasible for large-scale therapy or prophylaxis. In studies on the effect of oral immunoglobulin on rotavirus infection, daily doses in the interval of 600 to 9000 mg have been tried in clinical tests. Successful intervention has also been reported when treating *H. pylori* and cryptosporidial infections with daily administrations of 3 to 15 g immunoglobulin from immunized cows (Hammarström et al., Immunol Rev, 139 (1994) 43–70). Generally speaking, all studies hitherto point to the necessity of using high doses of immunoglobulins when trying to combat an ongoing infection. The need for more specific immunoglobuline preparations, allowing the use of smaller doses, is thus an urgent one.

To maximize the potency of an immunological regimen for the treatment and prevention of *H. pylori*, it is of great importance to find a specific conserved antigenic determinant, which plays a central role for the pathogenicity of *H. pylori*. Using such an antigenic determinant would make it possible to produce highly specific and therapeutically efficient novel polyclonal and/or monoclonal immunoglobulin preparations.

SUMMARY OF THE INVENTION

The above problem of providing specific, cost-efficient and therapeutically superior immunoglobulin preparations for the treatment and prevention of *H. pylori* has now been solved through the composition and methods according to the attached patent claims. The present inventors have now surprisingly shown, that highly specific and therapeutically efficient polyclonal and/or monoclonal immunoglobulin preparations can be provided through the immunization of an animal with an adhesin protein, specific for *H. pylori*. The invention will now be described in closer detail with reference to the attached, non-limiting figures and examples.

One objective of the present invention was to further purify and characterize the *H. pylori* blood group antigen binding (BAB) adhesin to make possible the development of methods and materials for specific and selective diagnosing and treatment of *H. pylori* induced infections and related diseases and the development of said methods and materials. A further and equally important objective was to determine the DNA sequences of the genes involved in the expression of this protein. These objectives were fulfilled through the protein, the DNA and the methods and materials specified herein. The DNA sequences are attached as SEQ ID NOS: 1 and 2, disclosing the babA and babB sequences, respectively. The full protein sequences are disclosed in SEQ ID NOS: 3 and 4.

DESCRIPTION OF THE FIGURES

FIGS. 4A–C shows receptor activity directed affinity tagging and protein purification of the BabA adhesin.

DESCRIPTION OF THE INVENTION

Figure 1A:
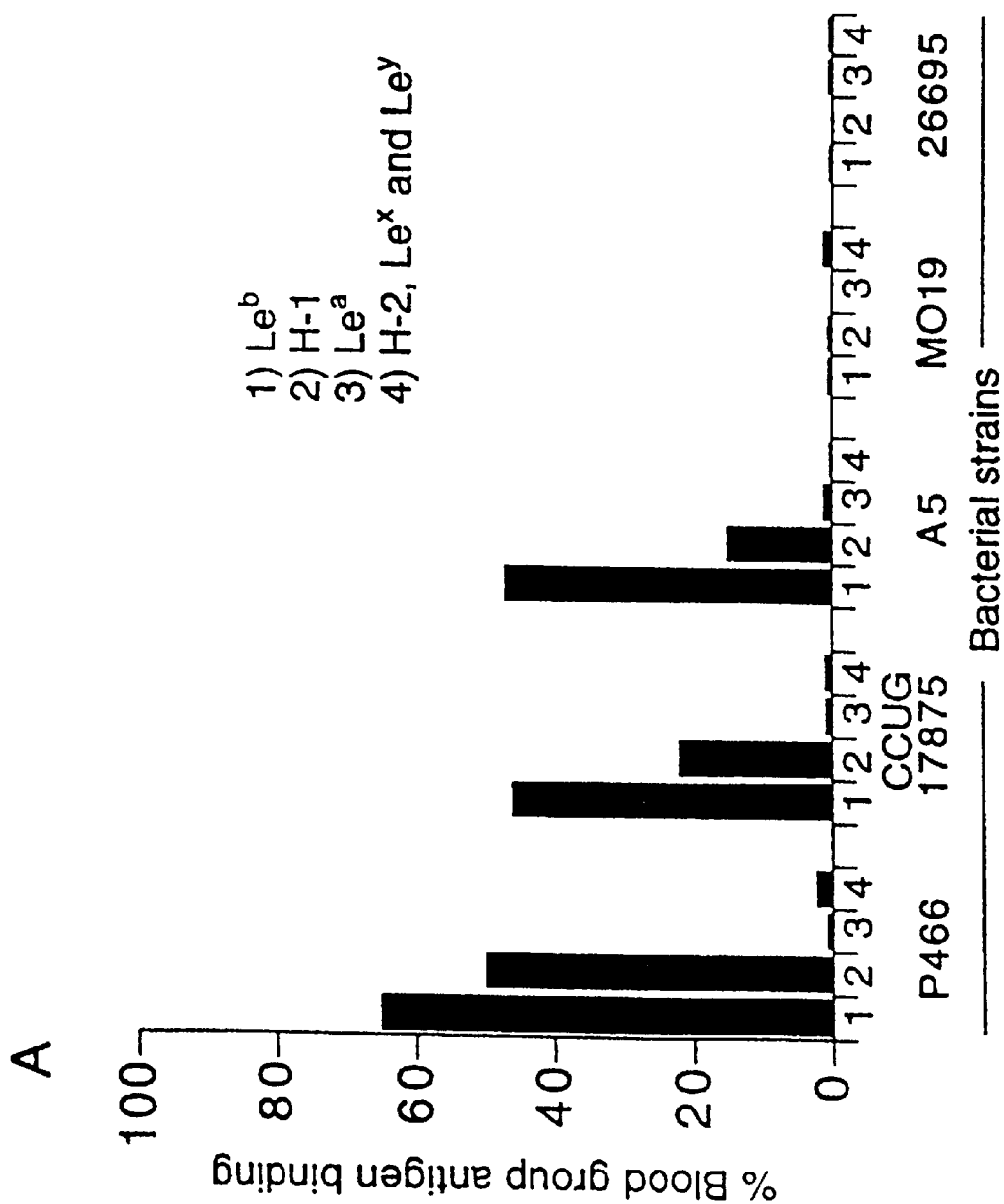
FIG. 1A) illustrates the bacterial binding to soluble blood group antigens. *H. pylori* strains were incubated with $^{125}$I-labeled blood group antigen glycoconjugates and bound $^{125}$I-activity was measured (Note the absence of blood group antigen binding shown for strains MO19 and 26695), FIG. 1B) illustrates an receptor displacement assay. Strain CCUG 17875 was first incubated with 10 ng $^{125}$I-labeled Le$^b$ antigen glycoconjugate and the complex was then challenged (1 h) with an excess of unlabeled Le$^b$ or Le$^a$ glycoconjugate, before the $^{125}$I-activity in the bacterial pellet was measured. Concentrations of the unlabeled glycoconjugate ranged from 50 ng to 8 μg and FIG. 1C) shows the results of a Scatchard analysis of the *H. pylori*-Le$^b$ antigen interaction. Bacterial binding to the Le$^b$ glycoconjugate was titrated to an affinity constant (Ka) value of $8 \times 10^{-10}$ M$^{-1}$ (13).

The blood group antigen binding adhesin, BabA, has now been biochemically characterized and purified by a novel technique, receptor Activity Directed Affinity Tagging (Retagging). Two genes, babA and babB were found to code for two different but very similar proteins. The present invention thus comprises a novel blood group antigen binding adhesin. The DNA sequences are disclosed in SEQ ID NO: 1 (babA) and SEQ ID NO: 2 (babB) The protein sequences are disclosed in SEQ ID NOS: 3 and 4. The invention also includes any pharmaceutical composition comprising said adhesin protein and/or fractions thereof. Examples of such pharmaceutical compositions are for example medicaments for the prevention or treatment of *Helicobacter pylori* induced gastritis, gastric and duodenal ulcers and gastric adenocarcinoma. Optionally said pharmaceutical composition additionally encompasses pharmaceutically acceptable excipients.

Further, the present invention comprises the BAB-adhesin gene or genes for expression of an adhesin protein according to the invention. Said invention also comprises a novel method for the isolation and purification of said adhesin. The disclosed genes are contemplated to function as a cassette system, the organism alternating between these to avoid immunity in the host. It is very likely, that homologies of the disclosed sequences exist and additionally supplement said cassette function in other strains of *H. pylori*. Also, genes corresponding to a homology of the first 40 amino acids or genes, corresponding to a homology of the last, about 300 amino acids, can function to this effect. It is further highly likely, that *Helicobacter pylori* is able to switch between several genes, similar to the disclosed genes, in a so-called cassette system.

The invention additionally comprises monospecific antisera produced using the novel adhesin protein and/or fractions thereof. Said monospecific antisera is preferably produced according to any suitable, conventional method for producing monospecific antisera in vitro or in vivo, e.g. by inoculating a suitable animal. Such methods are familiar to a person skilled in the art. Antibodies raised in a suitable animal or in the patient to be treated, can subsequently be administered locally, e.g. orally to the patient.

The invention further comprises the use of said monospecific antisera for the manufacturing of a test kit for quantitative or qualitative determinations of adhesin protein or fractions thereof in cells, tissues or body fluids.

The invention further comprises the use of said adhesin protein or corresponding DNA for use in therapy or immunisation and/or in the manufacture of compositions for said uses. The invention specifically encompasses the use of said DNA for immunisation therapy and for the manufacture for compositions for such therapy. Preferably, in an immunisation therapy where said composition is administered orally to a patient, the adhesin protein, fractions thereof or said DNA is administered in combination with a pharmaceutically suitable immunostimulating agent. Examples of such agents include, but are not limited to the following: cholera toxin and/or derivatives thereof, heat labile toxins, such as *E. coli* toxin and similar agents. The composition according to the present invention can further include conventional and pharmaceutically acceptable adjuvants, familiar to a person skilled in the art of immunisation therapy. Preferably, in an immunisation therapy using the inventive DNA or fractions thereof, said DNA is preferably administered intramuscularly, whereby said DNA is incorporated in suitable plasmide carriers. An additional gene or genes encoding a suitable immunostimulating agent can preferably be incorporated in the same plasmide.

Said immunisation therapies are not restricted to the above-described routes of administration, but can naturally be adapted to any one of the following routes of administration: oral, nasal, subcutaneous and intramuscular. Especially the oral and nasal methods of administration are promising, in particular for large-scale immunisations.

The present inventors have surprisingly shown, that highly specific and therapeutically efficient polyclonal and/or monoclonal immunoglobulin preparations can be provided through the immunisation of an animal with an adhesin protein or fractions thereof, specific for *H. pylori*. When considering immunisation against *H. pylori*, it is worth noting that the infection is known to be lifelong despite a vigorous immune response in the gastric mucosa. An increased local production of IgA in the mucosa is not necessarily enough and the administration of monospecific antibodies directed against a central virulens factor, such as the adhesin according to the present invention, may constitute a more effective approach.

The term "immunisation" refers here to a method for inducing a continuous high level of antibody and/or cellular immunresponse. The term "animal" here preferentially denotes any member of the subphylum Vertebrata, a division that includes all animals, including mammals, which are characterized by a segmented bony or cartilaginous spinal column. All vertebrates have a functional immune system and respond to antigens by producing antibodies. The term "protein" is used here to denote a naturally occurring polypeptide and the term "polypeptide" is used here in its widest meaning, i.e. any amino acid polymer (dipeptide or longer) linked through peptide bonds. Accordingly the term "polypeptide" comprises proteins, oligopeptides, protein fragments, analogues, muteins, fusion proteins and the like.

The term "antibody" as used in this context includes an antibody belonging to any of the immunological classes, such as immunoglobulins A, D, E, G or M. Of particular interest are nevertheless immunoglobulin A (IgA) since this is the principle immunoglobulin produced by the secretory system of warm-blooded animals. However, in cow colostrum, the main antibody class is IgG 1.

Borén et al. have recently isolated and characterized a Lewis[b] binding protein with a molecular weight of about 73500 Da (See the priority applications SE 9602287-6 and SE 9701014-4, which are referred to in their entirety). This adhesin protein is thought to be a conserved structure and specific for pathogenic strains of H. pylori. Said protein is specific for at least one of the H. pylori strains included in the following group: CCUG 17875, NCTC 11637, A5, P466, G109, G56, Ba 185, Ba 99, 931 and 932.

This adhesin protein or immunologically effective fractions thereof are characterized in that the following amino acid sequence (SEQ ID NO:5) included:

EDDGFYTSVGYQIGEAAQMV or homologues thereof.

The following DNA sequence (SEQ ID NO:6) or homologues thereof is included in DNA for expression of said adhesin protein or fractions thereof:

5'-GAAGACGACGGCTTTTACACAAGCGTAG-
GCTATCAAATCGGT GAAGCCGCTCAAATGGTA-3'

According to one embodiment of the invention, a pregnant mammal, preferably a cow or another suitable domestic animal, is immunised with said Lewis[b] binding adhesin protein or fractions thereof. The adhesin protein or fractions thereof is/are preferably injected intramuscularly or subcutaneously in the chosen animal, optionally together with suitable adjuvants. Examples of such adjuvants include, but are not limited to immunostimulating agents such as cholera toxin and/or derivatives thereof, heat labile toxins, such as E. coli toxin and similar, conventional agents, such as classical adjuvants including mineral and vegetable oils. Subsequent to the regimen of immunization, comprising a necessary amount of doses, including so called booster-doses, over a time span allowing for optimal immunoglobulin expression, milk or sera is collected from said animal. Preferably the cow colostrum, which is specially high in immunoglobulins, is collected. The specific immunoglobulin fraction according to the present invention is then separated and purified in a conventional manner, e.g. including separation of fats, protein precipitation and concentration by ultrafiltration.

According to another embodiment of the invention, a bird, preferably a chicken or another suitable domestic bird, is immunized with said Lewis[b] binding adhesin protein or fractions thereof. The adhesin protein or fractions thereof is preferably injected intramuscularly or subcutaneously in the chosen bird, optionally together with suitable adjuvants. Examples of such adjuvants include, but are not limited to immunostimulating agents such as cholera toxin and/or derivatives thereof, heat labile toxins, such as E. coli toxin and similar, conventional agents, such as classical adjuvants including mineral and vegetable oils. Subsequent to the regimen of inmmunization, comprising a necessary amount of doses, including so called booster-doses, over a time span allowing for optimal immunoglobulin expression, sera or eggs is/are collected from said animal. Preferably the egg yolk, which is specially high in immunoglobulins, is collected. The specific immunoglobulin fraction according to the present invention is then separated and purified in a conventional manner, e.g. including protein precipitation and ultrafiltration. Alternatively, the egg yolk being of high nutritional value in addition to containing a high titer of specific antibodies according to the present invention, can be administered as such.

According to a preferred embodiment of the present invention, monoclonal immunoglobulin is produced by establishing transgenic animals. Said transgenic animals can be chosen from the following group of species: mammals, e.g. cow, goat and rabbit, and birds: e.g. chicken, duck, turkey. The mammal most preferably used is cow and the most preferable bird is chicken. Further developments of transgenic animals such as mice and rats could also offer new possibilities. The choice of animal is naturally governed by availability and local adaptation.

According to one embodiment, a stock of transgenic animals according to the present invention, adapted to the local conditions, are kept locally, e.g. in villages in developing countries to function as local units for the production of immunoglobulins for oral administration. For example transgenic cows, goats or chicken are suitable for this purpose and preferably chicken are used. Consumption of the milk or preferably the eggs, produced by the transgenic animals, can help to eradicate presently very difficult infectious diseases, e.g. diseases caused by H. pylori.

According to yet another embodiment of the present invention, monoclonal antibodies can be produced using the hybridoma method. The hybridoma method is well known to a skilled worker in the field of biochemistry and it is described e.g. in Galfre, G. And Milstein, C., Preparation of monoclonal antibodies: strategies and procedures (Methods in Enzymology, 73:3–46, 1981). A suitable host animal is immunized with the Lewis[b] binding adhesin protein or fractions thereof. When the immunization is accomplished, the animal is sacrificed, spleen cells collected and fused with cells from a neoplastic cell line, preferably myeloma cells. By choosing the growth conditions, the successfully fused hybridoma cells can be selected. The monoclonal antibodies produced by the hybridoma cell line can then be administered orally in a regimen for treatment and/or prevention of H. pylori infections.

Preferably the polyclonal and/or monoclonal antibodies are purified prior to administration and, more preferably, admixed with pharmaceutically suitable carriers and/or adjuvants. Examples of suitable carriers are saline, pharmaceutically acceptable fats, oils, carbohydrates and proteins. The carrier or carriers is/are preferably chosen so that the solubility and absorption of the immunoglobulin in the mucus layer lining the stomach is enhanced. Using suitable adjuvants the stability, therapeutic efficiency and nutritional value of the composition can be improved. To improve stability under storage, the immnunoglobulin composition can be lyophilized. Regardless of the exact preparation and formulation, it is of central importance to avoid denaturating the immunoglobulins.

The higher specificity, exhibited by the immunoglobulin preparation of polyclonal and/or monoclonal antibodies according to the invention, makes it possible use substantially lower doses compared to those presently used, thus lowering the cost and improving the availability of the treatment. The use of specific, monoclonal antibodies can make it possible to further lower the doses. The doses are in all cases a function of the antibody titer of the preparation. A high titer naturally allows the use of lower doses.

According to one embodiment of the invention, an immunoglobulin preparation is manufactured as follows: an animal is immunized with a Lewis[b] binding adhesin protein or fractions thereof, expressed by *Helicobacter pylori*, the immunoglobulin fraction is isolated from a excretion of said animal and subsequently purified. The purified immunoglobulin composition is admixed with suitable carriers and adjuvants to form a immunoglobulin preparation for the prevention or treatment of *H. pylori* infections. In cases where the antibody titer is sufficiently high and the other constituents of the immunoglobulin composition isolated from the animal are harmless, for example in the case of colostrum from immunized cows or egg yolk from immunized chicken, there is always the option of administering the colostrum or egg yolk to the patient without any further treatment of the colostrum or egg yolk.

The immunoglobulin composition according to the invention is preferably administered orally to the patient, in the smallest therapeutically or prophylactically effective dose. Presently conceived are doses in the interval of 0.1 to 1000 mg/day, preferably in the interval of 0.1 to 100 mg/day. The chosen doses naturally depend on the antibody titer of the preparation in question. The exact doses and the regimen of administration can be chosen by the physician responsible for the patient, infected by *Helicobacter pylori*. Routine experimentation and later, with increasing experience of this method, empirical information will suffice to establish the required amount. Multiple dosages may be used, as needed, to provide the desired level of therapeutic or profylactic effect. The immunoglobulin preparations according to the present invention can also, being free from adverse side effects and imposing practically no danger of overdosing, be taken prophylactically or therapeutically by a person without medical supervision.

A therapeutical effect can be attained, except with the specific antibody according to the present invention, also with at least two Fab-fragments of said antibody. Said embodiment is also encompassed by the scope of the present invention.

According to yet another embodiment, avirulent microorganisms, preferably bacteria, are used as expression systems for the specific antibody according to the present invention. An "avirulent microorganism" in this context is a microorganism which has the ability to colonize and replicate in an infected individual, but which does not cause disease symptoms associated with virulent strains of the same species of microorganism. The definition inherent in the GRAS (Generally Regarded As Safe) concept can be applied here. A GRAS-organism is suitable for use according to the present invention, provided that the organism externalises the antibody or can be modified to this effect. The term "microorganism" as used herein includes bacteria, protozoa and unicellular fungi. Preferably, bacteria are used as expression systems, e.g. bacteria of the genus Lactobacillus, Streptococcus or Enterobacteriae. The above mentioned expression system can be utilised in vitro for the production of the specific antibody according to the present invention or, according to a further embodiment of the invention, the micro-organism constituting the expression system can be administered directly to the patient. The micro-organisms can be harvested and administered as such, but they are preferably mixed with a suitable carrier, mixed in a suitable foodstuff, lyophilised, encapsulated or treated in any other conventional way, used for the delivery of viable micro-organisms to the gastrointestinal tract.

According to yet another embodiment, avirulent microorganisms, preferably bacteria, are used as expression systems for the specific adhesin protein according to the present invention. An "avirulent microorganism" in this context is a microorganism which has the ability to colonize and replicate in an infected individual, but which does not cause disease symptoms associated with virulent strains of the same species of microorganism. The definition inherent in the GRAS (Generally Regarded As Safe) concept can be applied here. A GRAS-organism is suitable for use according to the present invention, provided that the organism externalises the adhesin protein or can be modified to this effect. The term "microorganism" as used herein includes bacteria, protozoa and unicellular fungi. Preferably, bacteria are used as expression systems, e.g. bacteria of the genus Lactobacillus, Streptococcus or Enterobacteriae. The above mentioned expression system can be utilised in vitro for the production of the specific adhesin according to the present invention or, according to a further embodiment of the invention, the micro-organism constituting the expression system can be administered directly to the patient. The micro-organisms can be harvested and administered as such, but they are preferably mixed with a suitable carrier, mixed in a suitable foodstuff, lyophilised, encapsulated or treated in any other conventional way, used for the delivery of viable micro-organisms to the gastrointestinal tract.

The exact doses and the regimen of administration of said micro-organisms can be chosen by the physician responsible for the patient, infected by *Helicobacter pylori*. Routine experimentation and later, with increasing experience of this method, empirical information will suffice to establish the required amount. Multiple dosages may be used, as needed, to provide the desired level of therapeutic or prophylactic effect. The avirluent micro-organism expressing the antibody or adhesin protein according to the present invention can also, being free from adverse side effects and imposing practically no danger of overdosing, be taken prophylactically or therapeutically by a person without medical supervision. A preferred carrier in this specific application is a foodstuff, e.g. a fermented product such as fermented cereal or dairy product.

The creation of previously mentioned expression systems and still earlier mentioned methods of creating hybridomas and transgenic animals can include steps involving recombinant DNA techniques. Recombinant DNA techniques are now sufficiently well known and widespread so as to be considered routine. In very general and broad terms, recombinant DNA techniques consist of transferring part of the genetic material of one organism into a second organism, so that the transferred genetic material becomes a permanent part of the genetic material of the organism to which it is transferred. Methods for achieving this are well known and the mere choice of specific methods for achieving the objectives, set out in the present description and claims, fall under the scope of the invention.

It is possible, that *H. pylori* alone or together with related slow-acting bacteria are involved in the genesis and aggravation of other chronic inflammatory diseases in the gastrointestinal tract. It is obvious for a skilled practitioner how to modify the present invention, within the scope of the claims, to gain utility in the treatment and/or prevention of such diseases. Examples of such diseases are ulcerative colitis, Crohn's disease, sarcoidosis, Wegener's granulomatosis and other vasculithic disorders, as well as various neoplasms, including carcinomas of the colon, pancreas and prostate.

EXAMPLES

*H. pylori* strain CCUG 17875 was obtained from CCUG, Göteborg, Sweden. Strain A5, a gastric ulcer isolate, from Astra Arcus, Södertälje, Sweden. Strains P466 and MO19 were described previously (Borén et. al, Science, 262, 1892(1993)). Strain 26695 came from Dr. K. A. Eaton, The Ohio State University and its genome was recently sequenced by TIGR, Rockville, Md., USA. The panel of 45 H. pylori clinical isolates came from the University Hospital in Uppsala, Sweden. Bacteria were grown at 37° C. in 10% CO2 and 5% O2 for 48 h.

All blood group antigen glycoconjugates used, i.e. semi-synthetic glycoproteins constructed by the conjugation of purified fucosylated oligosacharides to serum albumin were from IsoSep AB, Tullinge, Sweden. The RIA was performed according to Falk et al. (Meth. Enzymol., 236, 353, 1994) with some modifications; the H-1, $Le^b$, $Le^a$, H-2, $Le^x$ and $Le^y$ glycoconjugates were 125I-labeled by the Chloramine T method. 1 ml of bacteria (A600=OD 0.10) was incubated with 300 ng of 125I -labelled conjugate (i.e. an excess of receptors) for 30 min. in phosphate buffered saline (PBS), 0.5% albumin, 0.05% Tween-20 (BB-buffer). After centrifugation, 125I-activity in the bacterial pellet was measured by gamma scintillation counting.

In this study the present inventors' first biochemically characterized and identified the H. pylori blood group antigen binding adhesin, BabA. H. pylori strains were analysed for binding to soluble $^{125}$I-labeled fucosylated blood group antigens (FIG. 1A). Binding of these strains to the soluble blood group antigens correlate with adherence in situ. The prevalence of blood group antigen binding (BAB)-activity was assessed among 45 clinical H. pylori isolates and the majority of the isolates, 71%, express $Le^b$ antigen binding properties (data not shown). In contrast, none of the reference strains (FIG. 1A), or strains from the panel of 45 clinical isolates, bind to the $Le^a$, H-2, $Le^x$, or $Le^y$ antigens. These results support our previous findings of high receptor specificity for the $Le^b$ and H-1 blood group antigens and demonstrate the high prevalence of BAB activity among clinical isolates.

Based on the presence or absence of virulence factors such as the Cytotoxin associated gene A (CagA) and the Vacuolating cytotoxin A (VacA), H. pylori strains are classified as type I or type II strains. H. pylori isolates from patients with duodenal ulcers most often express the VacA and the CagA-proteins, i.e. type-I strains. By definition, type II strains express neither markers. Twenty-one clinical isolates previously defined for expression of CagA and VacA were analysed for $Le^b$ antigen binding properties. Expression of CagA was found to correlate with bacterial binding to the $Le^b$ antigen (Table 1). The cagA gene belongs to a 40 kb pathogenicity island that encodes components of secretion and transport systems. These findings could indicate functional crosstalk between the cag pathogenicity island and the BabA adhesin gene, for the correct presentation of the BabA adhesin protein in the bacterial outer membrane.

Figure 1B:
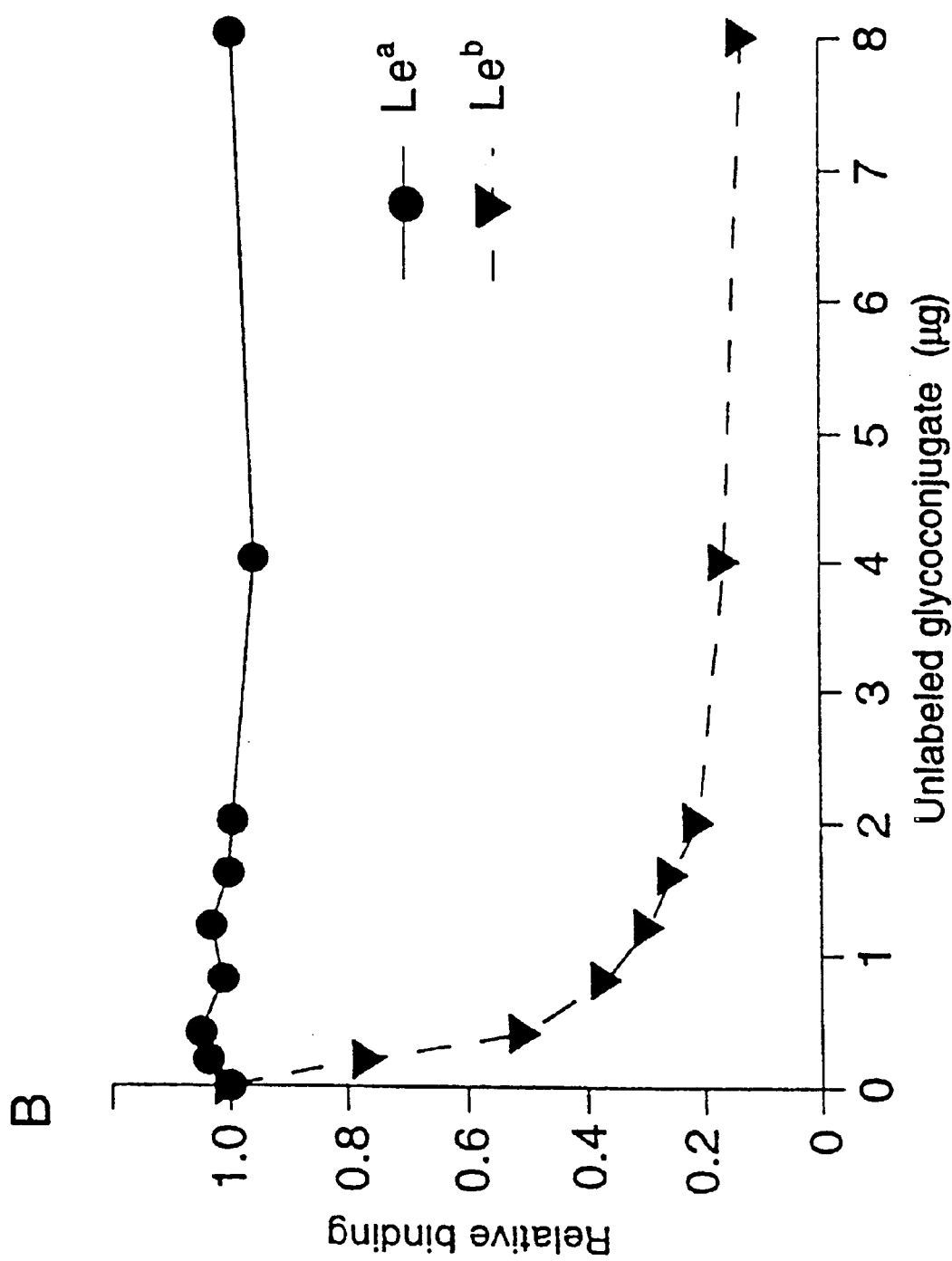
Figure 1C:
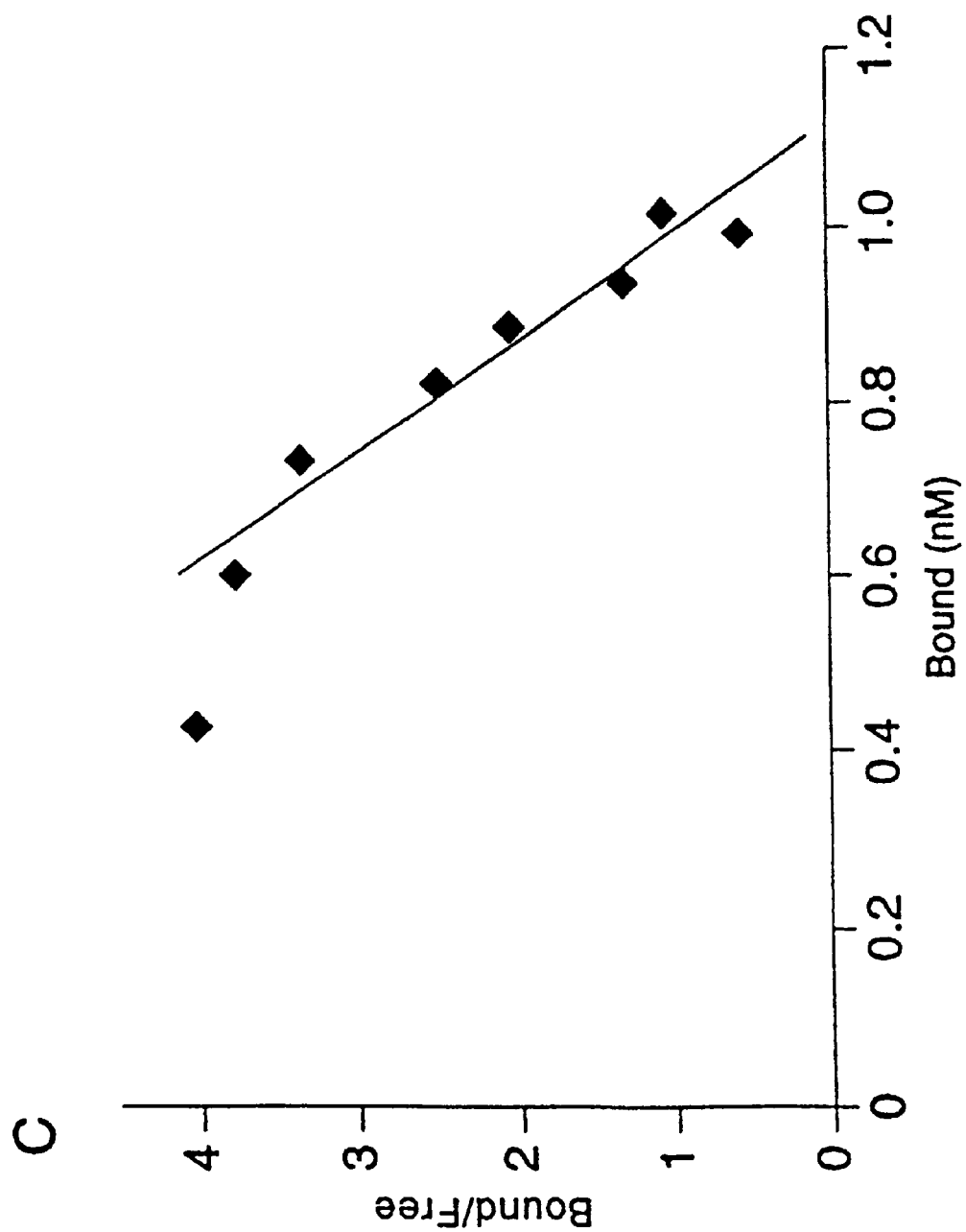

To further characterize BabA, the present inventors determined the affinity constant ($K_a$) between BabA and the $Le^b$ antigen. Since $K_a$-values are based on equilibrium conditions (13), the present inventors first analysed the interaction by performing receptor displacement analysis. H. pylori CCUG 17875 (positive for $Le^b$ binding, FIG. 1A) was first incubated with $^{125}$I-labeled $Le^b$ glycoconjugate. Then unlabeled $Le^b$ glycoconjugate was added in a dilution series. The unlabeled $Le^b$ conjugate displaced the bound $^{125}$I-labeled $Le^b$ glycoconjugate efficiently (FIG. 1B). The results demonstrate that the receptor-adhesin complex formed is in a true state of equilibrium. An equivalent excess of $Le^a$ glycoconjugate did not dissociate the $Le^b$-BabA complex, verifying the high receptor specificity (FIG. 1B). The $K_a$-value for the $Le^b$-BabA complex of strain CCUG 17875 was titrated with $Le^b$ glycoconjugate in concentrations from 10 ng to 260 ng/ml and determined to be of an high affinity close to $1\times10^{10}M^{-1}$ (FIG. IC). The number of $Le^b$ glycoconjugate molecules bound to BabA on the bacterial cell surface was calculated to be around 500 per cell. This number is similar to the number or fimbriae organelles on the surface of E. coli (14). However, for the BabA adhesin, the calculations are based on the assumption that the majority of bacterial cells in the experiment exhibit an equal number of adhesin molecules with $Le^b$ antigen binding properties.

TABLE 1

BAB activity among H. pylori Type I and Type II strains

| Type | Strain | BAB activity |
| --- | --- | --- |
| Type I | CCUG 17874 | − |
| CagA⁺, VacA⁺ | G39 | − |
|  | G11 | − |
|  | G20 | − |
|  | G27 | + |
|  | G56 | + |
|  | G106 | − |
|  | G109 | + |
|  | 932 | + |
|  | Ba185 | + |
|  | 87A300 | + |
| Type Ia | 931 | + |
| CagA⁺, VacA⁻ | Ba99 | + |
|  | Ba179 | + |
|  | Ba194 | + |
| Type Ib | G12 | − |
| CagA⁻, VacA⁺ |  |  |
| Type Id | G104 | − |
| ΔcagA, VacA⁺ | Tx30 | − |
| Type II | G21 | − |
| CagA⁻, VacA⁻ | G50 | − |
|  | G198 | − |

To determine the prevalence of BabA in the bacterial population, strain CCUG 17875 was incubated with $Le^b$ or $Le^a$ antigens, and bacterial binding activity was visualised by confocal fluorescence microscopy (FIG. 2, upper panel). The analyses demonstrate the high prevalence of BabA binding activity in the bacterial population to the $Le^b$ antigen (FIG. 2A, green staining) and the complete lack of binding to the $Le^a$ antigen (FIG. 2B, red counter staining).

Figure 2A:
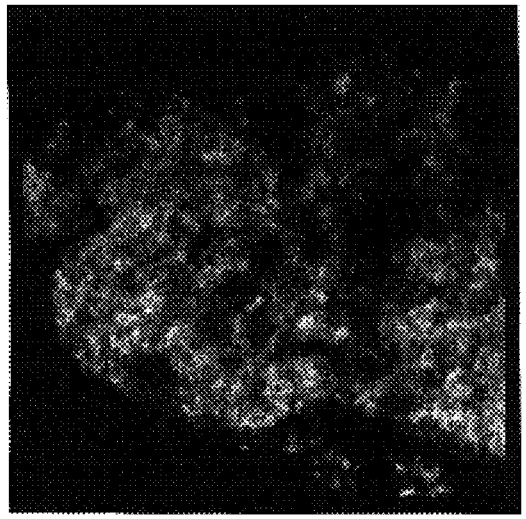
FIGS. 2A–D: Upper panel: Prevalence of the BabA adhesin in the bacterial population. Cells of strain CCUG 17875 were incubated with biotinylated Le$^b$ FIG. 2(A) or Le$^b$ FIG. 2(B) glycoconjugate. Bound biotinylated Lewis-conjugate was detected with FITC-labeled streptavidin (green fluorescence) and bacteria were counterstained with propidium iodine (red fluorescence). Lower panel: Localisation of the BabA adhesin. For electron microscopy (15) cells of strain CCUG 17875 were incubated with biotinylated Le$^b$ FIG. 2(C) or Le$^a$ FIG. 2(D).
Figure 2B:
Figure 2C:
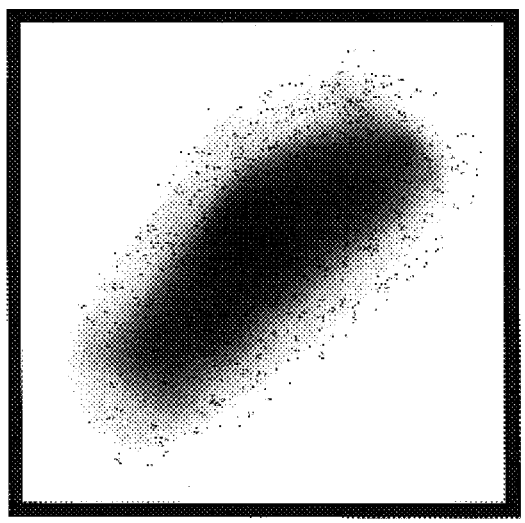
Figure 2D:
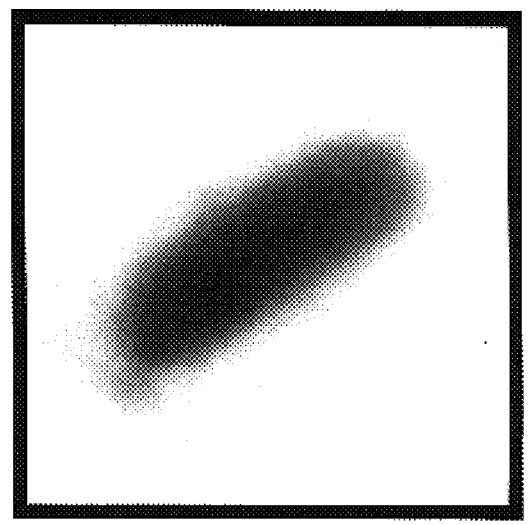

Next, the localisation and density of BabA on the bacterial cell surfaces was investigated by immunogold electron microscopy. The $Le^b$ antigen binding activity of the adhesin localised gold particles to the bacterial outer membrane (FIG. 2C). Individual bacterial cells exhibit an equal number of gold particles (data not shown). When the $Le^b$ antigen was substituted with the $Le^a$ antigen (lacking receptor activity), no gold particles were detected (FIG. 2D).

The molecular weight of BabA was characterized by receptor overlay analysis. A protein extract of strain CCUG 17875 was separated on SDS-PAGE and blotted to a membrane. The membrane was incubated with biotinylated $Le^b$ glycoconjugate, followed by detection with streptavidin and enhanced chemiluminescence. The BabA adhesin activity corresponds to a single 74 kDa band (FIG. 3A). The 40 kDa band is presumably endogenous peroxidase activity since it stains independently of the $Le^b$ conjugate overlay (lane 3). BabA was very heat stable and could regain some activity after heating to 97° C. (FIG. 3A, lane 2). The panel of strains exhibited the same molecular weight of BabA (FIG. 3B).

To purify BabA, a novel technique was developed, Receptor Activity Directed Affinity Tagging (ReTagging). Multifunctional crosslinking agents with radiolabeled donating tags have been previously used for receptor-ligand characterization studies. However, the use of affinity donating tags, such as biotin residues presented on flexible spacer structures, adds a new dimension to the applicability of crosslinker technology. An affinity tag, biotin, is transferred to the adhesin protein by the receptor activity and is used for further identification and for affinity purification of the adhesin part of the interaction, by streptavidin (FIGS. 4A, B).

A multi-functional crosslinking agent with a biotin donating handle was attached to the $Le^b$ glycoconjugate. The receptor activity of the $Le^b$ glycoconjugate subsequently directed the targeted biotin tagging of the BabA adhesin protein (FIGS. 4A, B). After crosslinking, the bacterial protein from strains A5, P466, and CCUG 17875 were separated on SDS-PAGE. Immunodetection with streptavidin demonstrated a biotin tagged protein, with the molecular weight of 74 kDa (FIG. 3C) (28), These results support the estimates of the molecular weight from the previous overlay analyses (FIG. 3B). Strain MO19 devoid of $Le^b$ antigen binding properties (FIG. 3B) (FIG. 1A), was negative for binding also in this set of analyses (FIG. 3C).

Figure 5:
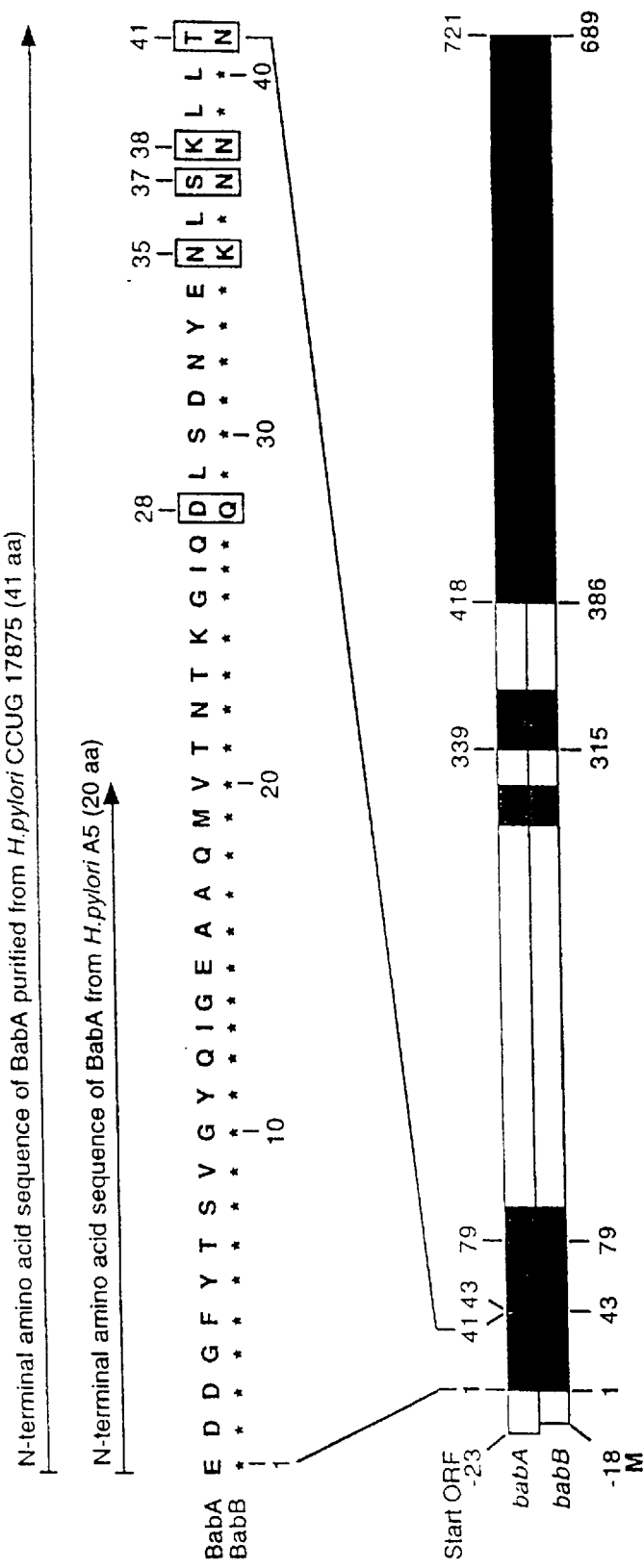
FIG. 5 shows the translated amino acid sequences for the babA and babB genes, corresponding to the N-terminal domain of the BabA (SEQ ID NOS: 7 and 8) adhesin.

The high specificity in the ReTagging technique provided a method for purification of the adhesin protein. Strains CCUG 17875 and A5, that both express the BabA adhesin (FIG. 1A) were processed by the ReTagging technique using crosslinker labelled $Le^b$ receptor conjugate as the biotin donor. After crosslinking, bacteria were suspended in SDS sample buffer. Streptavidin coated magnetic beads were subsequently added to the solubilised proteins, and biotin tagged BabA was extracted (FIG. 4C). The N-terminal 20 amino acid sequences of the BabA adhesins from strains CCUG 17875 (Australia) and A5 (Sweden) were found to be identical, indicating a biologically conserved protein (FIG. 5). Recently, a series of outer membrane proteins from *H. pylori* were characterized. These proteins, HopA-E, are homologous in their N-terminal sequences to BabA (17), possible indicating a motif for a common secretion mechanism. The biotin tagged BabA adhesin was purified more than 3000-fold from the cell extract, and the yield was calculated to 20%. However, based on data from the Scatchard plots, the level of available BabA adhesin would be about 5-times higher, i.e. approximately 1 mg adhesin/750 mg bacterial protein, which nevertheless could be the reason for the high signal to noise ratio (FIG. 3B). The purification of BabA via the ReTagging technique indicates the potential of this technique for the purification of lectins in complex receptor-ligand interactions, such as the selectin family of cell adhesion molecules.

Figure 3:
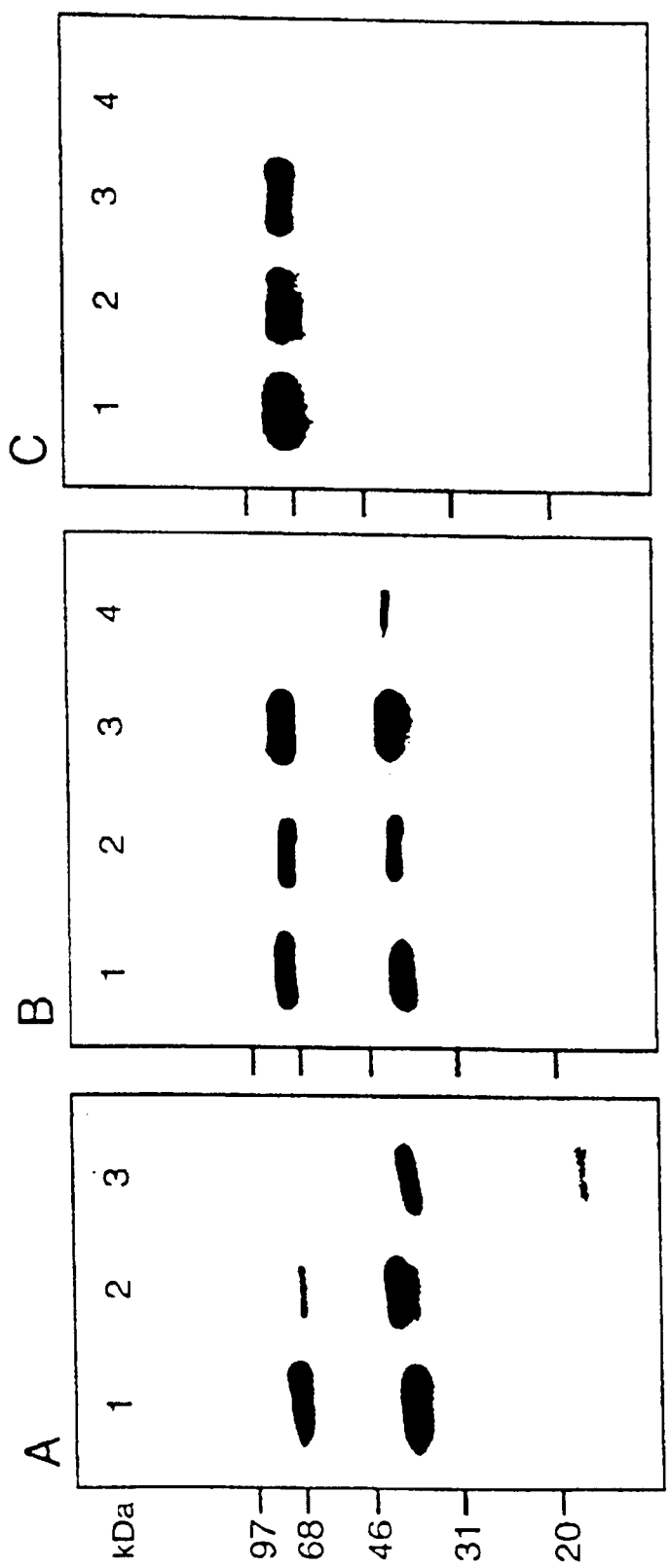
FIGS. 3A–C shows the characterization of the molecular weight of the BabA adhesin by the use of receptor overlay analysis FIGS. 3(A, B) and receptor activity directed affinity tagging of BabA FIG. 3(C).

To clone the gene encoding BabA, the N-terminal 20 aa sequence was utilised for the construction of degenerate primers (18). Two sets of clones were identified which both encode two different but very similar proteins. Both genes code for proteins having almost identical N-terminal domains and identical C-terminal domains, complicating the identification of the functional BabA gene. (FIG. 5). To identify the corresponding gene, the BabA adhesin was purified in large scale by ReTagging. This provided enough protein for an extended amino terminal sequence. 41 amino acids were identified and these residues unambiguously discriminated between the two genes by the differences in aa-positions 28, 35, 37, 38 and 41 (FIG. 5). The gene encoding BabA was named babA and correspond to a basic protein with a pI of 9.4 and a molecular weight of 78 kDa, i.e. of slightly higher molecular weight than that predicted from the SDS PAGE analyses (FIG. 3). The other gene, babB, corresponds to a protein of a calculated molecular weight of 75.5 kDa. In contrast to babA, the babB gene contains a predicted translational initiation codon (FIG. 5). This could indicate the existence of a third bab gene in the genome or mechanisms for recombination activities. Interestingly, the bab-genes were also detected in strains lacking Lewis b binding properties (data not shown). Gene cassette systems have been shown to promote antigenic variation in *Neisseria gonorrhoeae* (19). Another possibility would be the presence of similar genes coding for adhesins with differences in receptor specificity/host tissue tropism (20). Gene inactivation experiments targeting the bab-genes could aid in understanding this complex gene organisation.

Immunisation experiments with adhesins from *Bordetella pertussis* (21) indicate the potential for outer membrane proteins to act as vaccine candidates (discussed in ref 22). In a mouse model for persistent *H. pylori* infection, oral immunisation with *H. pylori* antigens proved protective against *H. pylori* infection (10). However, results from animal models are difficult to evaluate for human specific pathogens, such as *H. pylori* and Polio virus. For Polio, an animal model has been achieved by expressing the virus receptor in transgenic mice (23). A similar strategy was taken for *H. pylori*. A transgenic mouse was constructed by the use of an a1,3/4-fucosyltransferase, driving the synthesis of the human specific $Le^b$ antigen in the gastrointestinal tract (24). The Lewis b mouse can be useful for the evaluation of the role of the BabA adhesin as a colonisation/virulence factor and in addition for the evaluation of BabA as a vaccine candidate against acid peptic disease and gastric adenocarcinoma.

In the present study the ReTagging technique was used for the purification of the adhesin part of the microbial receptor-ligand interaction. By the use of purified adhesin/lectin-protein, the ReTagging technique could, in addition, be used to further study the receptor part of the interaction. Identification of the biologically active receptor structure, carrying $Le^b$ oligosaccharides, would aid in the understanding of the mechanisms supporting the chronic *H. pylori* infection.

Figure 6:
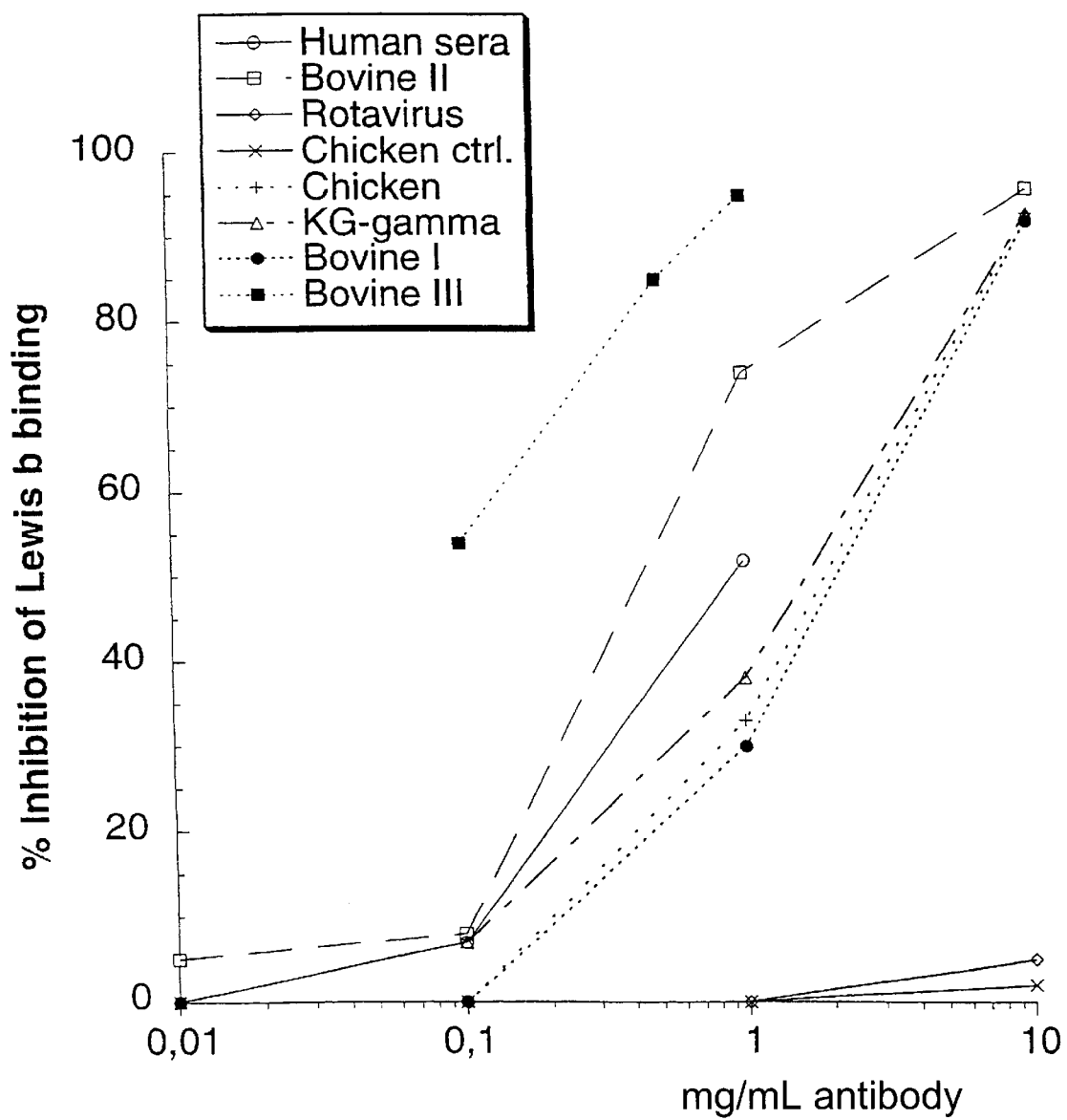
FIG. 6 shows the procentual inhibition of *H. pylori* binding to $^{125}$I-labeled Lewis b antigen for different preparations as a function of the antibody titre.

Inhibition of *H. pylori* binding to $^{125}$I-labeled Lewis b antigen by preparations is presented graphically, as a function of antibody concentration (mg/ml) in FIG. 6: 1 ml aliquots of *H. pylori* bacteria ($A_{600}$=OD 0.10) were pre-incubated with dilution series of antibody preparations, in 0.01–10 mg/ml for 2 hours in phosphate buffered saline (PBS), 0.5% albumin, 0.05% Tween-20™. Then 500 ng of $^{125}$I-labeled conjugate (i.e. an excess of receptor structure) was added and incubated for 30 minutes. After centrifugation, $^{125}$I-activity in the bacterial pellet was measured by gamma scintillation counting. The Lewis b blood group antigen glycoconjugates used, i.e. semi-synthetic glycoproteins constructed by the conjugation of purified fucosylated oligosaccharides to serum albumin were from IsoSep AB, Tullinge, Sweden.

Figure 7:
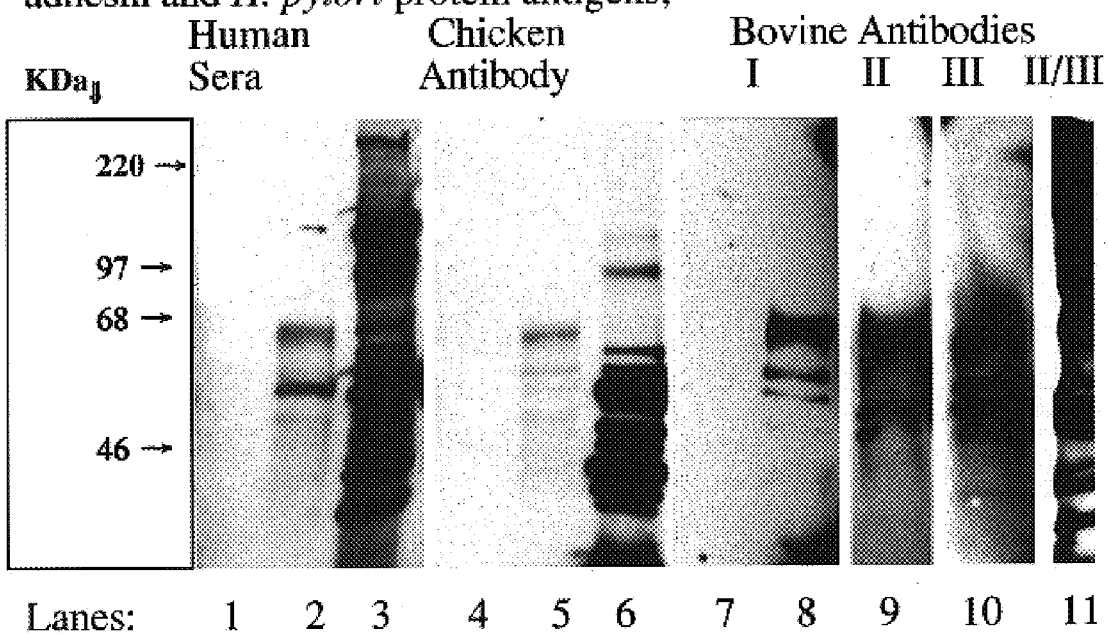
FIG. 7 shows a Western blot detection of the BabA adhesin by the different antibody preparations.

Western blot detection of the BabA adhesin by the different antibody preparations is presented in FIG. 7: Molecular weight rainbow marker (2 μL) from Amersham, Buckinghamshire, England, was dissolved in SDS sample buffer (lane 1). Approx. 100 ng of purified BabA adhesin (approx. 74 kDa with degradation product of approx. 55 kDa) was dissolved in SDS sample buffer (lane 2). SDS solubilized protein extracts of strain CCUG 17875 were prepared by dissolving the bacterial pellet corresponding to 0.15 ml of bacteria ($A_{600}$=OD 0.10) by SDS sample buffer (lane 3). The 3 protein samples were then boiled at 100° C. for 5 minutes. The proteins were separated on SDS-PAGE, and transferred to a PVDF-membrane for Western blot immuno analysis. Five sets of PVDF-membranes were prepared. The PVDF membranes were blocked/incubated overnight with 4% human sera/plasma, in phosphate buffered saline, from a patient with no *H. pylori* infection, i.e. with no serum antibodies against *H. pylori*. The membrane was then washed in phosphate buffered saline (PBS), 0.5% albumin, 0.05% Tween-20, followed by the addition of the antibody preparations. The sets of membranes were incubated with the following 5 antibody preparations; 1) pooled human sera from *H. pylori* infected patients, diluted 1:500. 2) Chicken antibodies (positive) 1 mg/ml diluted 1:100×, 3) Bovine I preparation of antibodies, 1 mg/ml diluted 1:100×. 4) Bovine II preparation of antibodies, 1 mg/ml diluted 1:100×. 5) Bovine III preparation of antibodies, 1 mg/ml diluted 1:100× (indicated in the figure). These antibodies were incubated with the membrane for 2 hours followed by extensive washings in phosphate buffered saline (PBS), 0.05% Tween-20, followed by the addition of secondary anti-human, anti-chicken, and anti-bovine antibodies labeled with HRP-peroxidase (from DAKO, Denmark), all diluted 1:2000×. Membranes were incubated for 1 hour, followed by extensive washings in phosphate buffered saline (PBS), 0.05% Tween-20. The membranes were developed with enhanced chemoluminescens (ECL) from Amersham. The results show, that the antigenic response against the adhesin is strongly enchanced in the bovine preparations. This finding is also supported by the inhibition data in FIG. 6.

Figure 8:
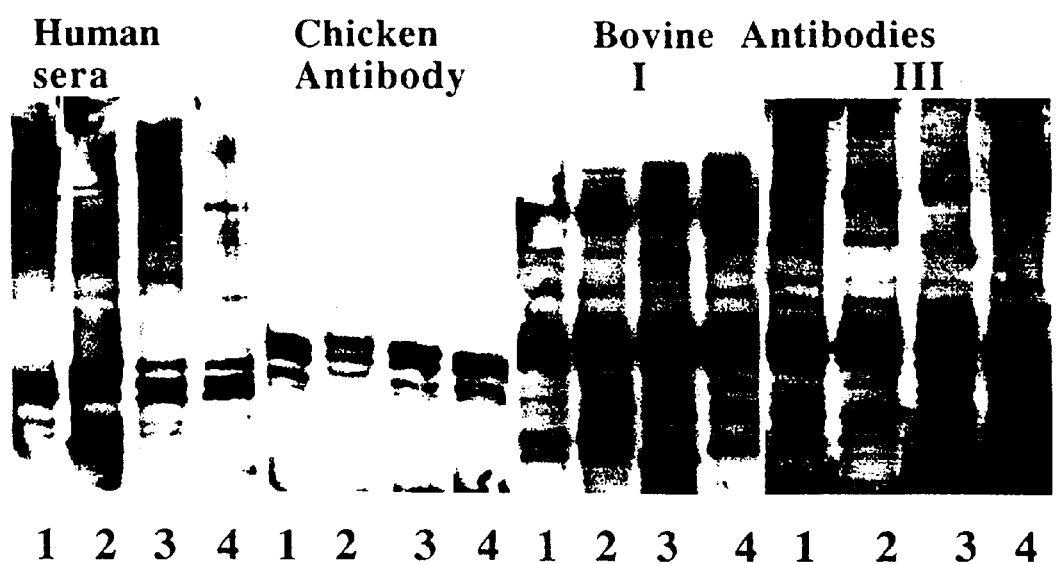
FIG. 8 shows four Western blot analyses of *H. pylori* proteins by the different antibody preparations.

Western blot analyses of *H. pylori* proteins by the different antibody preparations are shown in FIG. 8. 2 clinical isolates (1–2) from Dr. Lars Engstrand, Department of Clinical Microbiology and Cancerepidemiology, University Hospital, Uppsala, Sweden and strain CCUG 17875 (3), from Culture Collection, University of Göteborg, Department of Clinical Bacteriology, Göteborg, Sweden, and strain 52 (4) from Prof. Torkel Wadström, Dept. Medical Microbiology, Lunds University, were prepared for SDS-PAGE electrophoresis. Bacterial pellets corresponding to 0.15 ml of bacteria ($A_{600}$=OD 0.10) were dissolved in SDS sample buffer and heated to 100° C. for 5 minutes. The proteins were separated on SDS-PAGE, and transferred to PVDF-membranes for Western blot immuno analysis. The western blot analyses were as described above, i.e. the sets of membranes were incubated with the following 4 antibody preparations; 1) pooled human sera from *H. pylori* infected patients, diluted 1:500. 2) Chicken antibodies (positive) 1 mg/ml diluted 1:100×, 3) Bovine I preparation of antibodies, 1 mg/ml diluted 1:100×. 4) Bovine III preparation of antibodies, 1 mg/ml diluted 1:100× (indicated in the figure). These antibodies were incubated with the membrane for 2 hours followed by extensive washings in phosphate buffered saline (PBS), 0.05% Tween-20, followed by the addition of secondary anti-human, anti-chicken, and anti-bovine antibodies labeled with HRP-peroxidase (from DAKO, Denmark), all diluted 1:2000×. Membranes were incubated for 1 hour, followed by extensive washings in phosphate buffered saline (PBS), 0.05% Tween-20. The membranes were developed with enhanced chemoluminescens (ECL) from Amersham. The results show, that the chicken antibodies and the bovine preparations reacts nearly identically against all four strains, indicating conserved properties in strains of different geographical origin.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES AND NOTES

1. J. R. Warren, *Lancet,* i, 1273, 1983, B. Marshall, *Lancet,* i, 1273, 1983.
2. A. Dubois, *Emerging Infectious Diseases* 1, 79 (1995).
3. M. J. Blaser, *Sci. Amer.* 2, 92 (1996).
4. 3. M. J. Blaser, *Trends Microbiol.* 7, 255 (1993), D. E. Kirschner and M. J. Blaser, *J. Theor. Biol.* 176, 281 (1995).
5. P. Falk, T. Borén, and S. Normark, *Meth. Enzymol.* 236, 353 (1994).
6. D. G. Evans, D. J. Evans Jr., J. J. Moulds and D. Y. Graham, *Infect. Immun.* 56, 2896 (1988), S. Hirmo, M. Utt, M. Ringner and T. Wadström, *FEMS Immunol. and Med Microbiol.* 10, 301 (1995), T. Saitoh, et al *FEBS Lett.* 282, 385 (1991).
7. T. Borén, P. Falk, K. A. Roth, G. Larson, and S. Normark, *Science.* 262, 1892 (1993), P. Falk, et al *Proc. Natl. Acad. Sci. U.S.A.* 90, 2035 (1993).
8. *H. pylori* strain CCUG 17875 was obtained from CCUG, Göteborg, Sweden. Strain A5, a gastric ulcer isolate, came from Astra Arcus, Södertälje, Sweden. Strains P466 and MO19 were described previously (7). Strain 26695 came from Dr. K A. Eaton, The Ohio State University, and its genome was recently sequenced by The Institute for Genomic Research (TIGR), Rockville, Md. (J.-F. Tomb, et al, abstract 3B: 059, IX International Workshop on Gastroduodenal Pathology and *Helicobacter pylori,* Copenhagen, Denmark, 1996). The panel of 45 *H. pylori* clinical isolates came from the University Hospital in Uppsala, Sweden. Bacteria were grown at 37(C. in 10% $CO_2$ and 5% $O_2$ for 48 h.
9. All blood group antigen glycoconjugates used, i.e. semisynthetic glycoproteins constructed by the conjugation of purified fucosylated oligosaccharides to serum albumin (7, 25), were from IsoSep AB, Tullinge, Sweden. The RIA was performed according to ref. 26 with some modifications; The H-1, Le$^b$, Le$^a$, H-2, Le$^x$, and Le$^y$ glycoconjugates were $^{125}$I-labeled by the Chloramine T method. 1 ml of bacteria ($A_{600}$=OD 0.10) was incubated with 300 ng of $^{125}$I-labeled conjugate (i.e. an excess of receptors) for 30 min. in phosphate buffered saline (PBS), 0.5% albumin, 0.05% Tween-20 (BB-buffer). After centrifugation, $^{125}$I-activity in the bacterial pellet was measured by gamma scintillation counting.
10. A. Covacci, et al, *Proc. Natl. Acad. Sci. U.S.A.* 90, 5791 (1993), M. Marchetti, et al, *Science* 267, 1655 (1995).
11. S. Censini et al, *Proc. Natl. Acad. Sci. U.S.A.* 93, 14648, (1996).
12. Z. Xiang, et al, *Infect. Immun.* 63, 94 (1995).
13. A. G. Scatchard, *Ann. N. Y. Acad. Sci.* 51, 600 (1949).
14. O. Mol, and B. Oudega, *FEMS. Microbiol. Reviews,* 19, 25 (1996).
15. Confocal microscopy was performed on a Nikon/Multiprobe 2001 instrument (Molecular Dynamics, Sunnyvale, Calif.). Electron microscopy was performed on a JEOL 100 CX instrument.
16. J. Brunner, *Trends in Cell Biol.* 6, 154 (1996), J. D. Bleil and P. M. Wassarman, *Proc. Natl. Acad. Sci. U.S.A.* 87, 5563, (1990).
17. M. M. Exner, P. Doig, T. J. Trust, and R. E. W. Hancock, *Infect. Immun.* 63, 1567 (1995), P. Doig, M. M. Exner, R. E. W. Hancock and T. J. Trust, *J. Bacteriol.* 177, 5447 (1995).
18. The BabA N-terminal sequence analysis was used to make degenerate oligonucleotides, which were used in PCR to obtain an amplified fragment from the chromosome of the baba gene. A 59 bp fragment was identified and used as probe for the screening of a low-copy plasmide (pACYC184) library of Sau3A partially digested chromosomal DNA from strain CCUG 17875.

19. P. Hagblom, E. Segal, E. Billyard, and M. So, *Nature*, 315, 156 (1985), R. Haas and T. F. Meyer, *Cell*, 44, 107 (1986).
20. A.-B. Jonsson, D. Ilver, P. Falk, J. Pepose, and S. Normark, *Mol. Microbiol*, 13, 403 (1994), N. Strömberg, P. G. Nyholm, I. Pascher, and S. Normark, *Proc. Natl. Acad. Sci USA* 88, 9340 (1991).
21. A. Kimura, K. T. Mountzouros, D. A. Relman, S. Falkow, J. L. Cowell, *Infect. Immun.* 58, 7 (1990).
22. T. Borén, and P. Falk, *Sci. Amer., Sci. & Med.* 4 (1994), L. S. Tompkins and S. Falkow, Science 267, 1621 (1995).
23. R. B. Ren, et al, *Cell* 63, 353 (1990).
24. P. G. Falk, L. Bry, J. Holgersson, and J. I. Gordon, *Proc. Natl. Acad. Sci. U.S.A.* 92, 1515 (1995).
25. P. D. Rye, *Nature Biotechnology.* 2, 155 (1996).
26. P. Falk, T. Borén, D. Haslam, M. G. Caparon, *Meth. Cell Biol.* 45, 161 (1994)
27. Cell extracts were prepared in SDS sample buffer without mercapto ethanol and heated at 37° C. or 97° C. for 10 min. before separation on SDS-PAGE. Proteins were blotted onto a PVDF membrane. The membrane was incubated with 1 μg/ml biotinylated Le$^b$ glycoconjugate or biotinylated albumin (negative control) overnight, labelled as described in ref 7. After washing in PBS/0.05% Tween-20, the biotinylated structures bound by the BabA band were probed by HRP-streptavidin and detected using ECL reagents (Amersham, Buckinghamshire, England).
28. The bacterial suspension was incubated with Le$^b$ glycoconjugate, to which the Sulfo-SBED crosslinker (Pierce, Rockville, Ill.) had been conjugated by the N-hydroxysuccinimide ester (NHS), according to the manufacturers specifications. The aryl azide crosslinker group was activated by UV irradiation (360 nm). Bacteria were washed with PBS pH 7.6, 0.05% Tween-20 and protease inhibitors (EDTA and benzamidine) under reducing conditions with 50 mM dithiothreitol (DTT). Bacterial proteins were separated on SDS-PAGE, and the biotin tagged BabA protein was detected by immunodetection (PVDF membrane/HRP-streptavidin and ECL) (FIG. 3C).
29. Strains CCUG 17875 and A5 were first processed by crosslinking and DTT treatment, as above (28), followed by solubilisation in SDS sample buffer. The biotin tagged BabA protein was then extracted with streptavidin coated magnetic beads (Advanced Magnetics Inc., Cambridge, Mass.). The beads were boiled in SDS sample buffer, and bound proteins were eluted and alkylated. The protein preparation was further fractionated by preparative SDS-PAGE (Prep-Cell 491, BioRad, Hercules, Calif.). Fractions with the biotin tagged protein, i.e. the BabA fractions, were identified by immunodetection using streptavidin/ECL. The pooled BabA preparation was then separated on SDS-PAGE and transferred to PVDF membrane. The BabA band was excised and the BabA protein was N-terminally sequenced using a Procise™ 494 instrument (Applied Biosystems, Foster City, Calif.).

What is claimed is:

1. An isolated and purified bacterial blood group anitgen binding adhesin protein (BabA) from *Helicobacter pylori* species, wherein said protein binds specifically to fucosylated Lewis$^b$ type I and H-1 blood group anitgen-glycoconjugates and, wherein said protein contains less than 20% bacterial protein impurities, has a molecular weight in the interval of 73 to 75 kDa as determined by sodium dodecyl sulfate-polyacrylamide gel electrophoresis (SDS-PAGE), and is not a HopA, HopB, HopC, HopD, or HopE protein.

2. The adhesion protein of claim 1, wherein the SEQ ID NO:5

EDDGFYTSVGYQIGEAAQMV is in an amino terminal position.

3. The adhesion protein of claim 1, wherein the protein has a molecular weight of about 73.5 kDa, as determined by SDS-PAGE.

4. The adhesion protein of claim 3, wherein said *Helicobacter pylori* species is *Helicobacter pylori* strain CCUG 17875.

5. An immunogenic composition comprising an adhesion protein according to any one of claim 1, 2, 3, or 4, optionally together with pharmaceutically acceptable excipients.

* * * * *